US008491210B2

(12) United States Patent
Jimenez et al.

(10) Patent No.: US 8,491,210 B2
(45) Date of Patent: Jul. 23, 2013

(54) ORAL CARE SYSTEM, KIT AND METHOD

(75) Inventors: Eduardo Jimenez, Manalapan, NJ (US); Sharon Kennedy, Randallstown, MD (US); Robert Moskovich, East Brunswick, NJ (US); John Gatzemeyer, Hillsborough, NJ (US); Joachim Storz, Zell am See (AT); Raimund Klausegger, Vienna (AT)

(73) Assignee: Colgate-Palmolive Company, New York, NY (US)

( * ) Notice: Subject to any disclaimer, the term of this patent is extended or adjusted under 35 U.S.C. 154(b) by 311 days.

(21) Appl. No.: 12/883,693

(22) Filed: Sep. 16, 2010

(65) Prior Publication Data

US 2011/0135379 A1 Jun. 9, 2011

Related U.S. Application Data

(60) Provisional application No. 61/242,954, filed on Sep. 16, 2009.

(51) Int. Cl.
*A46B 11/00* (2006.01)

(52) U.S. Cl.
USPC ............... 401/123; 401/280; 15/167.1

(58) Field of Classification Search
USPC ....... 401/118–125, 268–280; 15/167.1–167.3
See application file for complete search history.

(56) References Cited

U.S. PATENT DOCUMENTS

| 64,732 | A | 5/1867 | Wylie |
| 261,456 | A | 7/1882 | Hoffman |
| 766,556 | A | 8/1904 | Symonds |
| 1,062,480 | A * | 5/1913 | Larocque ................. 401/47 |
| 1,244,324 | A | 10/1917 | Hackley |
| 1,292,416 | A | 1/1919 | Auld |

(Continued)

FOREIGN PATENT DOCUMENTS

| CN | 201025977 | 2/2008 |
| DE | 29613012 | 10/1966 |

(Continued)

OTHER PUBLICATIONS

Partial International Search Report from the International Searching Authority [EP] from corresponding International Application No. PCT/US2010/049102 dated Dec. 22, 2010.

(Continued)

*Primary Examiner* — David Walczak
*Assistant Examiner* — Jennifer C Chiang
(74) *Attorney, Agent, or Firm* — Ryan M. Flandro

(57) ABSTRACT

An oral care system and method wherein a dispenser is mounted to the handle of an oral care implement. The dispenser holds an oral care material and is alterable between a storage state wherein a dispensing end of the dispenser nests within the handle and an application state wherein the dispensing end of the dispenser is un-nested and exposed for oral care use. In one aspect, the invention is an oral care system comprising: an oral care implement comprising a head, a handle having a longitudinal axis, and one or more oral surface engaging elements; a dispenser having a reservoir containing an oral care material and an applicator for dispensing the oral care material; the dispenser alterable between: (i) a storage state wherein the applicator is nested within the handle; and (ii) an application state wherein the applicator is un-nested from the handle and exposed for oral care use.

28 Claims, 8 Drawing Sheets

U.S. PATENT DOCUMENTS

| | | |
|---|---|---|
| 1,546,516 A | 7/1925 | Smith |
| 1,555,064 A | 9/1925 | La Mothe |
| 1,668,511 A | 5/1928 | McLaughlin |
| 1,701,030 A | 2/1929 | Collins |
| 1,746,474 A | 2/1930 | Hogner |
| 1,913,528 A | 6/1933 | White |
| 1,975,723 A | 10/1934 | Johnssen |
| 2,068,213 A | 1/1937 | Wilson |
| 2,247,003 A * | 6/1941 | Smith et al. ............... 401/191 |
| D134,723 S | 9/1942 | Riksheim |
| 2,356,874 A | 8/1944 | Nageotte |
| 2,637,060 A | 3/1946 | Cowan |
| 2,399,660 A | 5/1946 | Boulicault |
| 2,437,769 A | 3/1948 | Traylor |
| 2,438,641 A | 3/1948 | Loehr |
| 2,445,571 A | 7/1948 | Fuston |
| 2,448,033 A | 8/1948 | Kruck |
| 2,521,882 A | 9/1950 | Swift et al. |
| 2,541,949 A | 2/1951 | Thacker et al. |
| 2,579,899 A | 12/1951 | Burrows |
| 2,670,881 A | 3/1954 | Sjoblom |
| 2,676,568 A | 4/1954 | Maczynski |
| 2,718,299 A | 9/1955 | Atwater et al. |
| 2,771,858 A | 11/1956 | Cribbs et al. |
| 2,800,899 A | 1/1957 | Barron |
| 2,845,645 A | 8/1958 | Wishnefsky et al. |
| 2,885,110 A | 5/1959 | Tregilgas |
| 2,885,116 A | 5/1959 | Tregilgas |
| 2,968,827 A | 1/1961 | Leo et al. |
| 3,108,687 A | 10/1963 | Dayton |
| 3,148,684 A | 9/1964 | Keeler |
| 3,181,539 A | 5/1965 | Aston |
| 3,187,758 A | 6/1965 | Eklund |
| 3,215,320 A | 11/1965 | Heisler et al. |
| 3,293,749 A | 12/1966 | George et al. |
| 3,296,642 A | 1/1967 | Aylott |
| 3,358,699 A | 12/1967 | Bau |
| 3,359,991 A | 12/1967 | Spatz |
| 3,359,992 A | 12/1967 | Cishek et al. |
| 3,378,176 A | 4/1968 | Snyder |
| 3,406,694 A | 10/1968 | Odence |
| 3,468,612 A | 9/1969 | Aston |
| 3,683,924 A | 8/1972 | Louie |
| 3,910,706 A | 10/1975 | Del Bon |
| 3,986,645 A | 10/1976 | Baldwin et al. |
| 4,201,491 A | 5/1980 | Kohler |
| 4,275,750 A | 6/1981 | Clark |
| 4,277,194 A | 7/1981 | Smith |
| 4,296,518 A | 10/1981 | Furrier et al. |
| 4,323,157 A | 4/1982 | Idec |
| 4,331,267 A | 5/1982 | Duncan et al. |
| 4,340,367 A | 7/1982 | Vadas et al. |
| 4,350,712 A | 9/1982 | Kocharian et al. |
| 4,384,645 A | 5/1983 | Manfredi |
| 4,413,760 A | 11/1983 | Paton |
| 4,506,810 A | 3/1985 | Goncalves |
| 4,527,574 A | 7/1985 | Manfredi |
| 4,543,679 A | 10/1985 | Rosofsky et al. |
| 4,573,820 A | 3/1986 | Kirchhoff |
| 4,582,059 A | 4/1986 | Tiwari |
| 4,594,015 A | 6/1986 | Pomares |
| 4,641,766 A | 2/1987 | Vlasich |
| 4,655,372 A | 4/1987 | Ross et al. |
| 4,659,327 A | 4/1987 | Bennett et al. |
| 4,662,385 A | 5/1987 | Schefer |
| 4,763,815 A | 8/1988 | Von Schuckmann et al. |
| 4,767,032 A | 8/1988 | Smith |
| 4,776,717 A | 10/1988 | Iizuka et al. |
| 4,808,022 A | 2/1989 | Iizuka et al. |
| 4,826,341 A | 5/1989 | Kwak |
| 4,865,481 A | 9/1989 | Scales |
| 4,866,809 A | 9/1989 | Pelletier |
| 4,874,117 A | 10/1989 | Kay et al. |
| 4,879,781 A | 11/1989 | Desimone |
| 4,886,186 A | 12/1989 | Andris |
| 4,887,924 A | 12/1989 | Green |
| 4,892,427 A | 1/1990 | Ford |
| D310,308 S | 9/1990 | Wolsey |
| 4,954,000 A | 9/1990 | Gueret |
| 4,997,299 A | 3/1991 | Ohba |
| 5,000,356 A | 3/1991 | Johnson et al. |
| 5,011,317 A | 4/1991 | Gueret |
| 5,016,782 A | 5/1991 | Pfanstiel |
| 5,018,892 A | 5/1991 | Krueckel et al. |
| 5,028,158 A | 7/1991 | Fey |
| 5,066,155 A | 11/1991 | English et al. |
| 5,156,479 A | 10/1992 | Iizuka |
| 5,199,807 A | 4/1993 | Uchida |
| 5,217,475 A | 6/1993 | Kuber |
| 5,234,136 A | 8/1993 | Kopis |
| 5,244,298 A | 9/1993 | Greenhouse |
| 5,249,876 A | 10/1993 | Hattman |
| 5,294,205 A | 3/1994 | Moeck et al. |
| 5,336,005 A | 8/1994 | Moeck et al. |
| 5,403,105 A | 4/1995 | Jameson |
| 5,423,623 A | 6/1995 | Bakic |
| 5,425,591 A | 6/1995 | Contreras et al. |
| 5,454,660 A | 10/1995 | Sakurai et al. |
| 5,540,361 A | 7/1996 | Fattori |
| 5,547,302 A | 8/1996 | Dornbusch et al. |
| 5,560,518 A | 10/1996 | Catterall et al. |
| 5,569,278 A | 10/1996 | Persad |
| 5,573,341 A | 11/1996 | Iaia |
| 5,608,940 A | 3/1997 | Panyon, Jr. |
| 5,611,687 A | 3/1997 | Wagner |
| 5,695,788 A | 12/1997 | Woods |
| 5,697,531 A | 12/1997 | Fattori |
| 5,709,004 A | 1/1998 | Paduano et al. |
| 5,725,133 A | 3/1998 | Iaia |
| 5,733,058 A | 3/1998 | Hofmann |
| 5,765,573 A | 6/1998 | Gueret |
| 5,772,347 A | 6/1998 | Gueret |
| 5,791,801 A | 8/1998 | Miller |
| 5,803,640 A | 9/1998 | Nakajima et al. |
| 5,827,002 A | 10/1998 | Nakajima |
| 5,827,308 A | 10/1998 | Thakur et al. |
| 5,839,622 A | 11/1998 | Bicknell et al. |
| 5,851,079 A | 12/1998 | Horstman et al. |
| 5,860,572 A | 1/1999 | Harrold et al. |
| 5,862,817 A | 1/1999 | Lee |
| 5,879,095 A | 3/1999 | Gueret |
| 5,893,860 A | 4/1999 | Ripich et al. |
| 5,911,532 A | 6/1999 | Evancic |
| 5,916,228 A | 6/1999 | Ripich et al. |
| 5,941,254 A | 8/1999 | Heler |
| 5,955,114 A | 9/1999 | Llanos |
| 5,970,990 A | 10/1999 | Dunton et al. |
| 5,980,145 A | 11/1999 | Griffith |
| 5,996,850 A | 12/1999 | Morali et al. |
| 6,015,293 A | 1/2000 | Rimkus |
| 6,039,053 A | 3/2000 | Turrentine |
| 6,056,469 A | 5/2000 | Algorri |
| 6,056,763 A | 5/2000 | Parsons |
| 6,070,598 A | 6/2000 | Gueret |
| 6,071,026 A | 6/2000 | Martinez et al. |
| 6,082,918 A | 7/2000 | Gueret |
| 6,086,276 A | 7/2000 | Gueret |
| 6,099,315 A | 8/2000 | Markowitz |
| 6,200,055 B1 | 3/2001 | Fusaro, Jr. |
| 6,202,247 B1 | 3/2001 | Lorenz, Jr. |
| 6,210,061 B1 | 4/2001 | Johnson |
| 6,213,662 B1 | 4/2001 | Aljanedi |
| 6,220,773 B1 | 4/2001 | Wiegner et al. |
| 6,224,573 B1 | 5/2001 | Yeager et al. |
| 6,227,209 B1 | 5/2001 | Kim et al. |
| 6,238,117 B1 | 5/2001 | Griebel et al. |
| 6,290,417 B1 | 9/2001 | Kaminski |
| 6,325,076 B1 | 12/2001 | Ramirez |
| 6,331,085 B1 | 12/2001 | Schrepf et al. |
| 6,345,629 B1 | 2/2002 | Vives |
| 6,363,949 B1 | 4/2002 | Brown |
| 6,368,001 B1 | 4/2002 | Roeder |
| 6,398,439 B1 | 6/2002 | Szekely |
| 6,406,694 B1 | 6/2002 | LaRosa |
| 6,439,885 B2 | 8/2002 | Antler |
| 6,440,149 B1 | 8/2002 | Potti |
| 6,450,716 B1 | 9/2002 | Szekely |

| | | |
|---|---|---|
| 6,475,172 B1 | 11/2002 | Hall |
| 6,488,427 B1 | 12/2002 | Breidenbach et al. |
| 6,592,281 B2 | 7/2003 | Clark et al. |
| 6,607,323 B2 | 8/2003 | Breidenbach et al. |
| 6,647,581 B1 | 11/2003 | Persad et al. |
| 6,648,641 B1 | 11/2003 | Viltro et al. |
| 6,672,783 B1 | 1/2004 | Licata et al. |
| 6,688,317 B2 | 2/2004 | Gueret |
| 6,688,793 B2 | 2/2004 | Goyet |
| 6,688,796 B1 | 2/2004 | Liu |
| 6,745,781 B2 | 6/2004 | Gueret |
| 6,746,170 B2 | 6/2004 | Delage |
| 6,752,558 B1 | 6/2004 | Hsu |
| 6,824,018 B1 | 11/2004 | Eaddy et al. |
| 6,866,438 B2 | 3/2005 | Bauer et al. |
| 6,880,999 B2 | 4/2005 | Biegel et al. |
| 6,918,511 B1 | 7/2005 | Spatz et al. |
| 6,923,587 B2 | 8/2005 | Lee |
| 6,957,753 B2 | 10/2005 | Tani |
| 7,029,484 B2 | 4/2006 | Ripich |
| 7,044,671 B2 | 5/2006 | Parikh et al. |
| 7,051,642 B2 | 5/2006 | Kageyama |
| 7,055,527 B2 | 6/2006 | Tien |
| 7,086,564 B1 | 8/2006 | Corrigan |
| 7,086,796 B2 | 8/2006 | Severa |
| 7,089,564 B2 | 8/2006 | Chen et al. |
| 7,114,505 B2 | 10/2006 | Bauer et al. |
| 7,143,462 B2 | 12/2006 | Hohlbein |
| 7,144,175 B2 | 12/2006 | Biegel |
| 7,168,435 B2 | 1/2007 | Vieu et al. |
| 7,192,212 B2 | 3/2007 | Gutberlet et al. |
| 7,201,527 B2 | 4/2007 | Thorpe et al. |
| 7,210,870 B2 | 5/2007 | Breidenbach et al. |
| 7,217,054 B2 | 5/2007 | Noguchi |
| 7,226,231 B2 | 6/2007 | Py et al. |
| 7,237,974 B2 | 7/2007 | Pfenniger et al. |
| 7,237,975 B2 | 7/2007 | Noguchi |
| 7,264,471 B2 | 9/2007 | Malcmacher |
| 7,293,928 B2 * | 11/2007 | Lane ........................ 401/184 |
| 7,303,348 B2 | 12/2007 | Phipps et al. |
| 7,309,184 B2 | 12/2007 | Butcher et al. |
| 7,309,185 B2 | 12/2007 | Thorpe et al. |
| 7,331,731 B2 * | 2/2008 | Hohlbein et al. ............ 401/133 |
| 7,347,360 B2 | 3/2008 | Lasch et al. |
| 7,374,360 B1 | 5/2008 | Szekely |
| 7,396,180 B2 | 7/2008 | Bugla et al. |
| 7,399,133 B1 * | 7/2008 | Eversole ...................... 401/123 |
| 7,401,373 B2 | 7/2008 | Tybinkowski et al. |
| 7,461,988 B2 | 12/2008 | Albisetti |
| 7,465,113 B2 | 12/2008 | Gueret |
| 7,474,048 B2 | 1/2009 | Forrest et al. |
| 7,481,591 B2 | 1/2009 | Dumler |
| 7,520,406 B2 | 4/2009 | Jaichandra et al. |
| 7,540,054 B2 * | 6/2009 | Goldstein ...................... 15/111 |
| 7,557,936 B2 | 7/2009 | Dickinson |
| 7,614,811 B2 | 11/2009 | Kaufman et al. |
| 7,641,411 B2 | 1/2010 | Biegel |
| 7,651,291 B2 | 1/2010 | Py et al. |
| 7,665,923 B2 | 2/2010 | Py et al. |
| 7,677,827 B1 | 3/2010 | Manukian |
| 7,823,593 B2 | 11/2010 | Gueret |
| 8,016,507 B2 | 9/2011 | Wright |
| 2002/0054783 A1 | 5/2002 | Gueret |
| 2002/0073496 A1 | 6/2002 | Kim |
| 2003/0012594 A1 | 1/2003 | Andersen |
| 2003/0057236 A1 | 3/2003 | Delage |
| 2004/0028456 A1 | 2/2004 | Giraldo |
| 2004/0092981 A1 | 5/2004 | Barlow et al. |
| 2004/0237996 A1 | 12/2004 | Fischer et al. |
| 2004/0240928 A1 | 12/2004 | Trocino |
| 2005/0006409 A1 | 1/2005 | Ganzeboom |
| 2005/0026774 A1 | 2/2005 | Nolan |
| 2005/0036821 A1 | 2/2005 | Pfenniger et al. |
| 2005/0069372 A1 | 3/2005 | Hohlbein et al. |
| 2005/0199655 A1 | 9/2005 | Petit |
| 2006/0058821 A1 | 3/2006 | Jansheski |
| 2006/0207627 A1 | 9/2006 | Thorpe et al. |
| 2006/0233588 A1 | 10/2006 | Gueret |
| 2006/0260635 A1 | 11/2006 | Dabney |
| 2006/0269351 A1 | 11/2006 | Mcafee |
| 2006/0269354 A1 | 11/2006 | Lane |
| 2006/0272666 A1 | 12/2006 | Wyatt et al. |
| 2006/0275225 A1 | 12/2006 | Prencipe |
| 2007/0007302 A1 | 1/2007 | Jaichandra et al. |
| 2007/0079845 A1 | 4/2007 | Gueret |
| 2007/0227553 A1 | 10/2007 | Gueret |
| 2007/0231055 A1 | 10/2007 | Albisetti |
| 2007/0292194 A1 | 12/2007 | Albisetti et al. |
| 2008/0063464 A1 | 3/2008 | Prague |
| 2008/0089733 A1 | 4/2008 | Lochak |
| 2008/0101850 A1 | 5/2008 | Wojcik et al. |
| 2008/0118300 A1 | 5/2008 | Burrowes |
| 2008/0189888 A1 | 8/2008 | Hohlbein |
| 2008/0274066 A1 | 11/2008 | Montgomery |
| 2009/0074679 A1 | 3/2009 | Silverman |
| 2009/0254055 A1 | 10/2009 | Clarke |
| 2009/0261007 A1 | 10/2009 | Sanchez |
| 2009/0288262 A1 | 11/2009 | Hall |
| 2009/0317432 A1 | 12/2009 | Kergosien |
| 2010/0168638 A1 | 7/2010 | Korogi et al. |
| 2010/0240013 A1 | 9/2010 | Levine |
| 2010/0284726 A1 | 11/2010 | Ottaviani et al. |
| 2011/0308030 A1 | 12/2011 | Jimenez et al. |
| 2012/0114410 A1 | 5/2012 | Jimenez et al. |
| 2012/0163902 A1 | 6/2012 | Jimenez et al. |

FOREIGN PATENT DOCUMENTS

| | | |
|---|---|---|
| DE | 2725495 | 12/1977 |
| DE | 3832224 | 8/1989 |
| EP | 0308549 | 3/1989 |
| EP | 0385815 | 9/1990 |
| EP | 1506726 | 2/2005 |
| FR | 850458 | 12/1939 |
| FR | 907669 | 3/1946 |
| FR | 1596074 | 6/1970 |
| FR | 2597734 | 10/1987 |
| GB | 666082 | 2/1952 |
| GB | 792448 | 3/1958 |
| GB | 1190280 | 4/1970 |
| GB | 2307674 | 6/1977 |
| GB | 2085717 | 5/1982 |
| GB | 2280361 | 2/1995 |
| GB | 2393642 | 4/2004 |
| JP | 48-093167 | 12/1973 |
| NL | 2002311 | 6/2010 |
| WO | WO 93/03648 | 3/1993 |
| WO | WO 96/01579 | 1/1996 |
| WO | WO 98/09572 | 3/1998 |
| WO | WO 98/18695 | 5/1998 |
| WO | WO 01/00103 | 1/2001 |
| WO | WO 02/17967 | 3/2002 |
| WO | WO 2004/112637 | 12/2004 |
| WO | WO 2005/065737 | 7/2005 |
| WO | WO 2008/062935 | 5/2008 |
| WO | WO 2009/151455 | 12/2009 |
| WO | WO 2010/132590 | 11/2010 |
| WO | WO 2011/078863 | 6/2011 |
| WO | WO 2011/078864 | 6/2011 |
| WO | WO 2011/079027 | 6/2011 |
| WO | WO 2011/079028 | 6/2011 |
| WO | WO 2012/082102 | 6/2012 |
| WO | WO 2012/082183 | 6/2012 |
| WO | WO 2012/082185 | 6/2012 |

OTHER PUBLICATIONS

International Search Report in International Application No. PCT/US10/049102 mailed Jun. 8, 2011.
ISR and Written Opinion for PCT/US2009/069402 mailed on Jul. 23, 2010.
Written Opinion for PCT/US2009/069402 mailed on Dec. 16, 2011.
ISR and Written Opinion for PCT/US2009/069408 mailed on Jul. 23, 2010.
Written Opinion for PCT/US2009/069408 mailed on Dec. 16, 2011.
ISR and Written Opinion for PCT/US2010/060105 mailed on Aug. 30, 2011.
ISR and Written Opinion for PCT/US2010/060861 mailed on Jun. 8, 2011.

ISR and Written Opinion for PCT/US2010/060867 mailed on Oct. 14, 2011.
ISR and Written Opinion for PCT/US2010/060874 mailed on Jan. 11, 2012.
ISR and Written Opinion for PCT/US2010/060877 mailed on Oct. 7, 2011.
ISR and Written Opinion for PCT/US2010/060881 mailed on May 16, 2011.
Written Opinion for PCT/US2010/060881 mailed on Dec. 28, 2011.
ISR and Written Opinion for PCT/US2011/023356 mailed on Oct. 21, 2011.
ISR and Written Opinion for PCT/US2011/045010 mailed on Jan. 25, 2011.
ISR and Written Opinion for PCT/US2011/046132 mailed on Dec. 1, 2011.
Written Opinion for PCT/US2011/046132, mailed Nov. 26, 2012.

\* cited by examiner

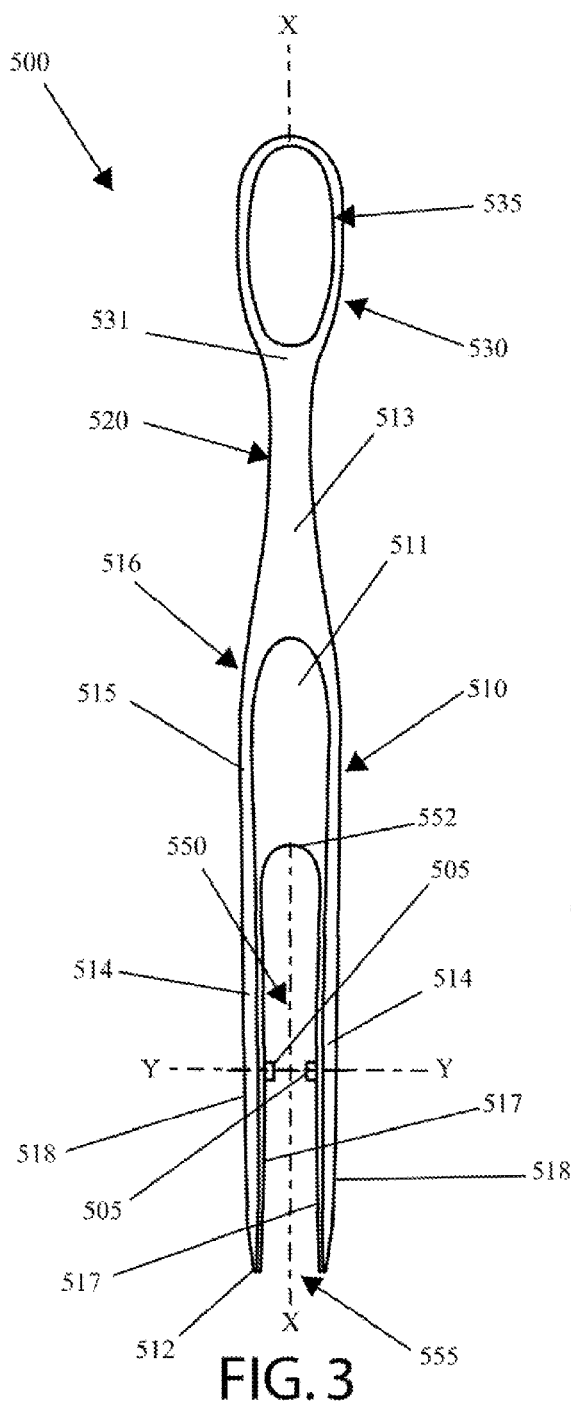
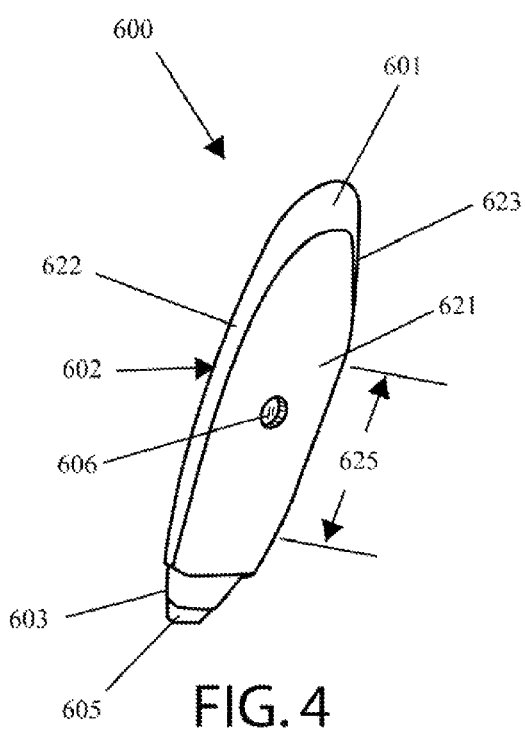
FIG. 3
FIG. 4

ORAL CARE SYSTEM, KIT AND METHOD

CROSS-REFERENCE TO RELATED PATENT APPLICATIONS

The present application claims the benefit of U.S. Provisional Patent Application No. 61/242,954, filed Sep. 16, 2009, the entirety of which is hereby incorporated by reference.

FIELD

The present invention relates generally to oral care systems, kits and methods of applying oral care materials, and specifically to an oral care system, kit and method including a toothbrush having a dispenser holding an oral care material built into a handle of the toothbrush. Suitable oral care materials include inactive and active agents, including without limitation, whitening agents, enamel strengthening or repair agents, tooth erosion preventing agents, and tooth sensitivity agents.

BACKGROUND

Oral care materials are applied in different ways. A common technique is to cast an impression of a person's teeth and provide a tray of the shape of this impression. A person then only needs to add an oral care material to the tray and to apply the tray to his/her teeth. This is left in place for a period of time and then removed. When the oral care material is a whitening agent, the teeth gradually whiten after a few treatments. Another technique is to use an oral care strip that has an oral care material on one surface. This strip is applied to a person's teeth and left in place for about 30 minutes. When the oral care material is a whitening agent, the teeth are gradually whitened after several applications. Yet another technique is to apply oral care materials to teeth using a small brush. This brush is repeatedly dipped back into the container or bottle during the application of the oral care material to ones teeth. When the oral care material is a whitening agent, the teeth gradually whiten after a few treatments.

A problem with existing brushing techniques is that saliva in the mouth contains the enzyme catalase. This enzyme will catalyze the decomposition of certain oral care materials, such as peroxides. The brush can pick up some catalase during the application of the oral care material and transport that catalase back to the bottle. This catalase now in the bottle can degrade the oral care material, such as peroxide, in the bottle. Another problem with this latter technique is that it does not adapt for use with certain oral care materials, such as anhydrous whitening compositions. In such situations, the brush may transport moisture in saliva from the mouth back into the bottle. This will have a negative affect on the oral care material, such as whitening composition by potentially decomposing the peroxide active ingredient. In addition, if a person washes the brush each time after use, moisture from the wet bristles can enter the bottle.

While tray-based systems are suitable, many people do not use them due to the fact that they tend to be uncomfortable and/or awkward. Moreover, in order to use a tray, a user must keep the tray and the required components at hand. This not only requires extra storage space in already cramped bathroom cabinets but also requires that the user remember to use the oral care system. Furthermore, these tray-based systems are not conveniently portable for transport and/or travel.

These problems require a better way to deliver an oral care material to the oral surface and a more convenient oral care system for transport and/or travel.

SUMMARY

The present invention is directed to an oral care system that utilizes an oral care implement, such as a toothbrush, having a dispenser containing an oral care material that is mounted to the handle of the toothbrush. In one preferred embodiment, the dispenser is pivotably mounted to the handle of the oral care implement and can be pivoted between: (i) a storage state wherein an applicator or dispensing end of the dispenser is nested within the handle; and (ii) an application state wherein the applicator or dispensing end is exposed for oral care use. The dispenser is preferably designed so as to blend into the handle and form a portion of the handle, thereby forming a handle that is shaped like a typical handle for an oral care implement, such as a toothbrush handle. The invention is particularly suited to be used with a tooth whitening agent and/or a tooth sensitivity agent. Of course, other oral care materials can be used.

In one aspect, the invention can be an oral care system comprising: a toothbrush comprising a head, a handle and one or more tooth engaging elements extending from the head; the handle having a distal end, a proximal end and a longitudinal axis; the handle of the toothbrush comprising a main body and a dispenser pivotably mounted to the main body; the dispenser including a housing having a first end and a second end, a reservoir located within the housing containing an oral care material, and an applicator at the second end of the housing for dispensing the oral care material from the reservoir; the main body including a base portion at the distal end of the handle and first and second flanges extending from the base portion to the proximal end of the handle, the first and second flanges extending along the longitudinal axis in a spaced apart manner so that a space is formed between an inner surface of the first flange and in inner surface of the second flange; the head connected to the base portion of the handle at the distal end; and the dispenser pivotably mounted between the first and second flanges within the space, the dispenser pivotable between: (i) a storage state wherein the applicator of the dispenser is nested within the main body; and (ii) an application state wherein the applicator is exposed for oral care use.

In another aspect, the invention can be a combined toothbrush and oral care material dispenser comprising: a toothbrush comprising: a handle having a proximal end, a distal end and a longitudinal axis; and a head connected to the distal end of the handle, the head including one or more tooth engaging elements extending from the head; a dispenser including: a housing having a dispensing end and a closed end; a reservoir located within the housing, the reservoir containing an oral care material; and an applicator at the dispensing end of the housing and in communication with the reservoir for dispensing the oral care material; the handle having an elongated slot extending along the longitudinal axis; and the dispenser pivotably mounted to the handle within the slot, the dispenser pivotable between: (i) a storage state wherein the applicator of the dispenser is nested within the handle; and (ii) an application state wherein the applicator is exposed for oral care use.

In yet another aspect, the invention can be an oral care system comprising: an ansate (i.e., provided with a handle) oral care implement comprising a head, a handle having a longitudinal axis, and one or more oral surface engaging elements; a dispenser having a reservoir containing an oral care material and an applicator for dispensing the oral care material from the reservoir; and the dispenser pivotably mounted to the handle, the dispenser pivotable between: (i) a storage state wherein the applicator of the dispenser is nested within the handle; and (ii) an application state wherein the applicator is exposed for oral care use.

In still another aspect, the invention can be a method of applying an oral care material to teeth comprising: providing an ansate oral care implement comprising a head, a handle having a longitudinal axis, and one or more tooth engaging elements, a dispenser having a reservoir containing the oral care material and an applicator for dispensing the oral care material from the reservoir, the dispenser pivotably mounted to the handle; cleaning the teeth with the tooth engaging elements of the ansate oral care implement while the dispenser is in a storage state wherein the applicator of the dispenser is nested within the handle; upon completion of the cleaning of the teeth, pivoting the dispenser to an application state wherein the applicator of the dispenser is exposed for oral care use; and applying the oral care material to the teeth by contacting the teeth with the applicator of the dispenser.

In an even further aspect, the invention can be a method of applying an oral care material to an oral surface comprising: a) providing an ansate oral care implement comprising a head, a handle having a longitudinal axis, and one or more oral surface engaging elements, a dispenser having a reservoir containing the oral care material and an applicator for dispensing the oral care material from the reservoir, the dispenser mounted to a portion of the handle; b) contacting the oral surface with the oral surface engaging elements while the dispenser is mounted to the portion of the handle and the applicator is nested within the handle; c) manipulating the dispenser so that the applicator is un-nested from the handle; and d) applying the oral care material to the oral surface through contact with the applicator.

BRIEF DESCRIPTION OF THE DRAWINGS

FIG. 3 is a front view of the toothbrush of the oral care system of FIG. 1, wherein the dispenser has been removed.

FIG. 4 is a perspective view of the dispenser of the oral care system of FIG. 1.

DETAILED DESCRIPTION

Figure 1:
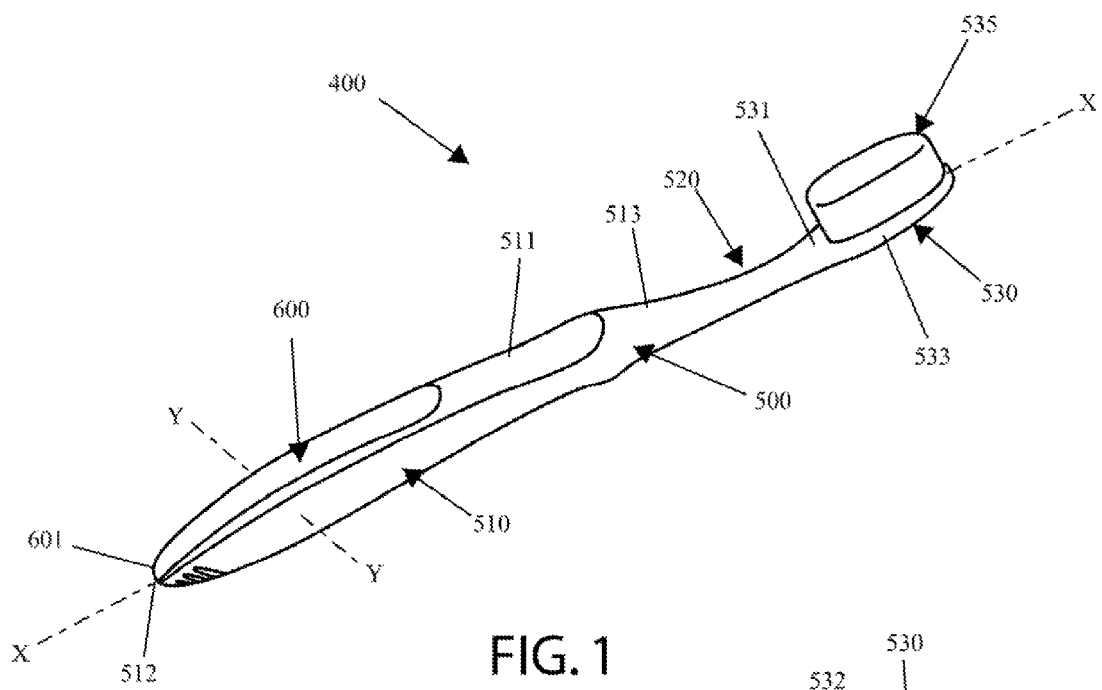
FIG. 1 is a front perspective view of an oral care system according to one embodiment of the present invention, wherein the dispenser is in a storage state.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the preferred embodiments. Accordingly, the invention expressly should not be limited to such preferred embodiments illustrating some possible non-limiting combination of features that may exist alone or in other combinations of features; the scope of the invention being defined by the claims appended hereto.

In the description of embodiments of the invention disclosed herein, any reference to direction or orientation is merely intended for convenience of description and is not intended in any way to limit the scope of the present invention. Moreover, the features and benefits of the invention are illustrated by reference to preferred embodiments. Accordingly, the invention expressly should not be limited to such preferred embodiments illustrating some possible but non-limiting combination of features that may be provided alone or in other combinations of features; the scope of the invention being defined by the claims appended hereto.

Preferred embodiments of the present invention will now be described with respect to one possible oral care or treatment system. Embodiments of the oral care system may include without limitation the following agents: tooth whitening, antibacterial, enamel protection, anti-sensitivity, anti-inflammatory, anti-attachment, fluoride, tartar control/protection, flavorant, sensate, colorant and others. However, other embodiments of the present invention may be used to store and dispense any suitable type of oral care agent and the invention is expressly not limited to any particular oral care system or agent alone.

Figure 2:
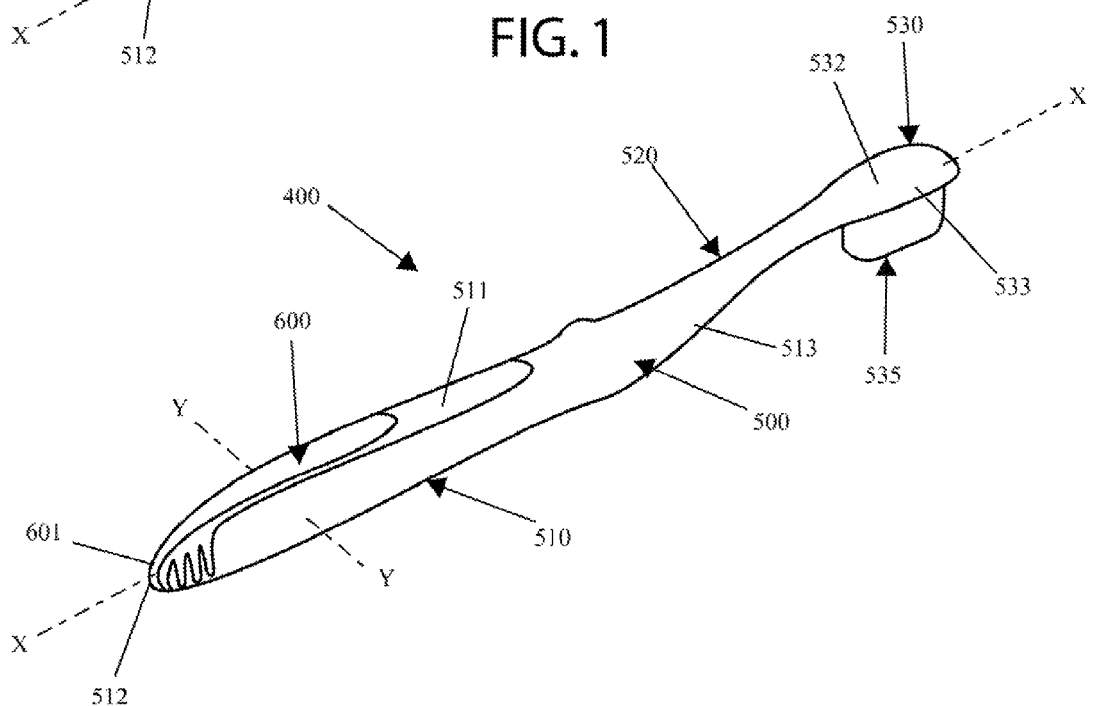
FIG. 2 is a rear perspective view of the oral care system of FIG. 1, wherein the dispenser is in a storage state.

Referring to FIGS. 1-2 concurrently, an oral care system 400 is illustrated according to one embodiment of the present invention. The oral care system 400 is a self-contained user-friendly system that comprises all of the necessary components and chemistries necessary for a user to perform a desired oral care routine. As will be described in greater detail below, the oral care system 400 generally takes the form of a modified toothbrush having a dispenser pivotally mounted within its handle. Because the dispenser nests flushly within the handle of the toothbrush itself, the oral care system 400 is portable for travel, is easy to use, and reduces the amount of required storage space.

The oral care system 400 generally comprises a toothbrush body 500 (hereinafter referred to simply as a toothbrush) and a dispenser 600. While the invention is described herein with respect to the use of a toothbrush as one of the two primary components of the oral care system 400, it is to be understood that other alternate oral care implements can be used within the scope of the invention, including tongue cleaners, tooth polishers and specially designed ansate implements having tooth engaging elements. In certain instances, the toothbrush 500 may include tooth engaging elements that are specifically designed to increase the effect of the oral car material in the dispenser on the teeth. For example, the tooth engaging elements may include elastomeric wiping elements that assist in removing stains from teeth and/or assist with forcing the oral care material into the tubules of the teeth. Moreover, while the toothbrush 500 is preferably a manual toothbrush, the toothbrush may be a powered toothbrush in other embodiments of the invention. It is to be understood that the inventive system can be utilized for a variety of intended oral care needs by filling the dispenser 600 with any oral care material, such as an oral care agent that achieves a desired oral effect. In one embodiment, the oral care agent, is preferably free of (i.e., is not) toothpaste as the dispenser is intended to augment not supplant the brushing regimen. The oral care agent and/or its medium can be selected to complement a toothpaste formula, such as by coordinating flavors, colors, aesthetics, or active ingredients.

The toothbrush 500 generally comprises a handle portion 510, a neck portion 520 and a head portion 530. The handle 510 provides the user with a mechanism by which he/she can readily grip and manipulate the toothbrush 500. The handle 510 may be formed of many different shapes, sizes, materials and a variety of manufacturing methods that are well-known to those skilled in the art, so long as it can pivotably mount the dispenser 600 as described in detail below. If desired, the handle 510 may include a suitable textured grip 511 made of soft elastomeric material. Suitable elastomeric materials include thermoplastic elastomers (TPE) or other similar materials used in oral care products. The elastomeric material may have a hardness durometer measurement ranging between A13 to A50 Shore hardness, although materials outside this range may be used. A preferred range of the hardness durometer rating is between A25 to A40 Shore hardness. While an over-molding construction can be utilized, a suitable deformable thermoplastic material, such as TPE, may be formed in a thin layer and attached with an appropriate adhesive or by other means.

The handle 510 can be a single or multi-part construction. The handle 510 extends from a proximal end 512 to a distal end 513 along a longitudinal axis X-X. As will be described in greater detail below, the dispenser 600, when in the storage state, nests flushly within the handle 510 of the toothbrush 600 and thereby forms a structural portion of the handle 510. To this extent, the closed end 601 of the dispenser 600 forms the proximal end 512 of the handle 510 of the toothbrush 500. The toothbrush 500 and the dispenser 600 are non-unitary separate structures that are specially designed to be pivotably mounted together.

The handle 510 transitions into the neck 520 at the distal end 513. While the neck 520 generally has a smaller transverse cross-sectional area than the handle 520, the invention is not so limited. The neck 520 is merely the transition region between the handle 510 and the head 530 and can conceptually be considered as a portion of the handle 510.

The head 530 and handle 520 of the toothbrush 500 are preferably formed as a single unitary structure using a molding, milling, machining or other suitable process. However, in other embodiments, the handle 510 and head 530 may be formed as separate components which are operably connected at a later stage of the manufacturing process by any suitable technique known in the art, including without limitation thermal welding, a tight-fit assembly, a coupling sleeve, adhesion, or fasteners. Whether the head 530 and handle 510 are of a unitary or multi-piece construction (including connection techniques) is not limiting of the present invention, unless specifically stated. In some embodiment of the invention, the head 530 may be detachable (and replaceable) from the handle 510 using techniques well-known in the art.

The head 530 generally comprises a front surface 531, a rear surface 532 and a peripheral surface 533. The front surface 531 and the rear surface 532 of the head 530 can take on a wide variety of shapes and contours, none of which are limiting of the present invention. For example, the front and rear surfaces 531, 532 can be planar, contoured or combinations thereof. Moreover, if desired, the rear surface 532 may also comprise additional structures for oral cleaning or tooth engagement, such as a soft tissue cleanser or a tooth polishing structure. An example of a suitable soft tissue cleanser is disclosed in U.S. Pat. No. 7,143,462, issued Dec. 5, 2006 to the assignee of the present application, the entirety of which is hereby incorporated by reference. An example of a tooth polishing structure can be an elastomeric element, such as a prophy cup(s) or elastomeric wipers. Furthermore, while the head 530 is normally widened relative to the neck 520 of the handle 510, it could in some constructions simply be a continuous extension or narrowing of the handle 510.

The front surface 531 comprises a collection of tooth engaging elements 535 extending therefrom for cleaning and/or polishing contact with an oral surface. While the collection of tooth engaging elements 535 is preferably suited for brushing teeth, the collection of cleaning elements 535 can also be used to polish teeth instead of or in addition to cleaning teeth. As used herein, the term "tooth engaging elements" is used in a generic sense to refer to any structure that can be used to clean, polish or wipe the teeth through relative surface contact. Common examples of "tooth engaging elements"

include, without limitation, bristle tufts, filament bristles, fiber bristles, nylon bristles, spiral bristles, rubber bristles, elastomeric protrusions, flexible polymer protrusions, combinations thereof and/or structures containing such materials or combinations. Suitable elastomeric materials include any biocompatible resilient material suitable for uses in an oral hygiene apparatus. To provide optimum comfort as well as cleaning benefits, the elastomeric material preferably has a hardness property in the range of A8 to A25 Shore hardness. One preferred elastomeric material is styrene-ethylene/butylene-styrene block copolymer (SEBS) manufactured by GLS Corporation. Nevertheless, SEBS material from other manufacturers or other materials within and outside the noted hardness range could be used.

The tooth engaging elements 535 of the present invention can be connected to the head 530 in any manner known in the art. For example, anchor free tufting (AFT) could be used to mount the cleaning elements. In AFT, a plate or membrane is secured to the brush head such as by ultrasonic welding. The bristles extend through the plate or membrane. The free ends of the bristles on one side of the plate or membrane perform the cleaning function. The ends of the bristles on the other side of the plate or membrane are melted together by heat to be anchored in place. Any suitable form of cleaning elements may be used in the broad practice of this invention. Alternatively, the bristles could be mounted to tuft blocks or sections by extending through suitable openings in the tuft blocks so that the base of the bristles is mounted within or below the tuft block.

In one embodiment, the tooth engaging elements 535 preferably include both a plurality of bristles for brushing teeth and elastomeric elements for polishing teeth. In one embodiment, a ring of elastomeric elements may be provided with a source of ultraviolet light located within the ring.

Figure 7:
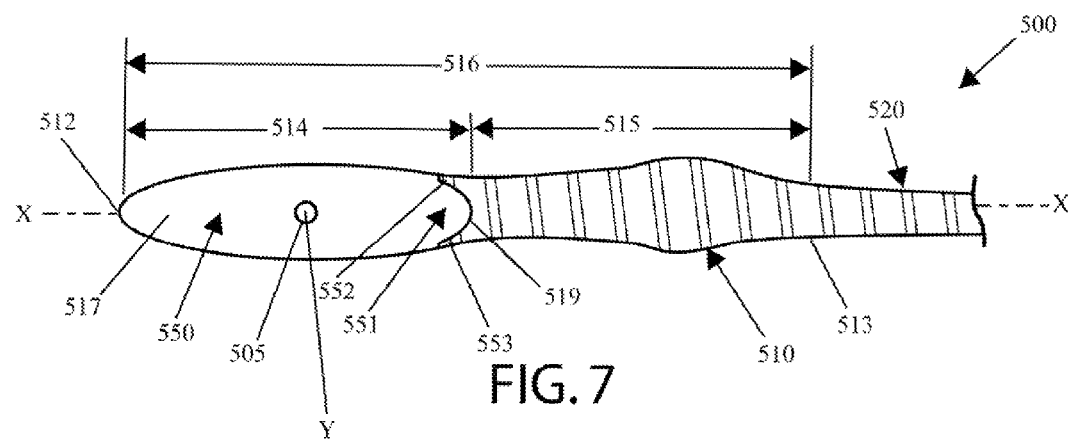
FIG. 7 is a longitudinal cross-sectional view of the handle portion of the toothbrush of the oral care system of the present invention along axis X-X of FIG. 3.

Referring now to FIGS. 3 and 7 concurrently, the toothbrush 500 of the oral care system 400 is illustrated wherein the dispenser 600 has been removed. The handle 510 of the toothbrush 500 is an elongated structure that extend along the longitudinal axis X-X. The handle 510 has a main body 516 that is preferably constructed of a hard structurally rigid material. Moldable thermoplastics are preferred. Suitable plastics include polymers and copolymers of ethylene, propylene, butadiene, vinyl compounds and polyesters such as polyethylene terephthalate.

The main body 516 of the handle 510 generally comprises two spaced apart flanges 514 and a base portion 515. The base portion 515 forms a distal portion of the main body 516 while the flanges 514 form a proximal portion of the main body 516. The base portion 515 is preferably of a solid construction for a majority of its length so as to provide structural stability and rigidity to the toothbrush 500. Of course, the invention is not so limited. In some embodiment, an aperture may be added to the base portion that holds an elastomeric gripping body having a centroid mass that shifts under pressure from a user's fingers.

The flanges 514 extend longitudinally from the base portion 515 toward the proximal end 512 of the toothbrush 500 in a substantially parallel arrangement to each other and to the longitudinal axis X-X. As a result, a space 550 is formed between the inner surfaces 517 of the flanges 514. The space 550 forms a slot that extends through the thickness of the handle 510 from the front surface to the rear surface, thereby forming a passageway through the handle 510. The space 550 is located at the proximal-most location along the handle 510, thereby forming an open ended slot. In other words, the space 550 has a transverse proximal opening 555 at the proximal end 512 of the toothbrush 500, the space 550 may be located at other longitudinal positions along the handle 510 as desired. For example, the space 550 could be centrally located along the handle 510 so that it is closed at both transverse ends. The space may even be in the neck portion 520. Furthermore, while the space 550 extends from the front surface to the rear surface of the handle 510, the space 550 can extend between the side surfaces of the handle 510 (left to right in FIG. 3).

The flanges 514 comprise substantially planar inner surface 517 and convexly curved outer surface 518. The convex outer surfaces 518 of the flanges 514 from a substantially smooth and uninterrupted contour with the contoured lateral surfaces of the base portion 515, thereby ensuring that the handle 510 appears as a typical toothbrush handle having a generally elliptical transverse cross-sectional profile along a majority of its length. This will be described in greater detail below with respect to FIG. 9.

A cavity 551 (which is in the form of an indent) is formed into in the transverse wall 519 of the body portion 515. The cavity 551 is in spatial communication with the space 550 that is formed between the flanges 514 and extends longitudinally along axis X-X from the space 550 toward the distal end 513 of the handle 510. As will be described in greater detail below, the cavity 551 acts as a nesting region for the applicator 605 of the dispenser 600 when the dispenser is in the storage state. As a result of the cavity 551 being in the form of an indent, top and bottom structural protrusions 552, 553 are formed. The protrusions 552, 553 can be formed from the hard plastic of the handle 510, the soft elastomeric material of the grip 511, and/or combinations thereof. Preferably, at least one of the protrusions 552, 553 is constructed so as to be sufficiently flexible so that the applicator 605 of the dispenser 600 can snap into and out of the cavity 551 by deforming the protrusions 552, 553 when rotated out of the storage state. Of course, the invention is not so limited and in some embodiments, one or more of the protrusions 552, 553 may be substantially inflexible or omitted all together.

Protuberances 505 are provided on and protrude from the inner surfaces 517 of the flanges 514. The protuberances 505 are aligned with each other along the axis Y-Y, which is oriented substantially perpendicular to the longitudinal axis X-X of the toothbrush 500. The protuberances 505 provide a pivoting structure that mates with depressions 606 formed into the dispenser 600, thereby forming a pivot joint when the oral care system 400 is fully assembled. This pivot joint facilitates the pivotable mounting of the dispenser 600 to the main body 516 of the handle 510 of the toothbrush 500. The axis Y-Y is the axis of rotation. While the protuberances 505 are in the form of cylindrical nubs, they can take on a wide variety of shapes and structures, including conical, rod-like, hemi-spherical, or irregular. Similarly, the depressions 606 of the dispenser 600 can take on any shape that matingly corresponds with the protuberances 505. Furthermore, while the pivot joint is exemplified as male protuberances 50 on the flanges 514 and female depressions 606 on the dispenser 600, the male/female structures could of course be alternated. Moreover, other styles of pivot joint could be used to pivotably mount the dispenser 600 to the toothbrush 500; including without limitation an axle, a ball joint, a magnetic pivot, a hinge and/or combinations thereof.

Figure 8:
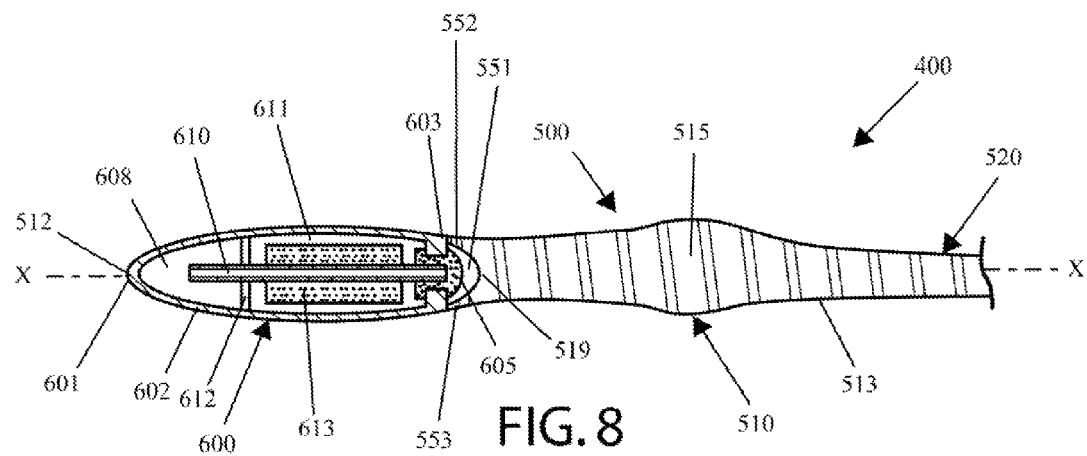
FIG. 8 is a longitudinal cross-sectional view of the oral care system of the present invention along line axis X-X of FIG. 1, wherein the dispenser is in the storage state.

Referring now to FIGS. 4 and 8 concurrently, the dispenser 600 is schematically illustrated. The dispenser 600 is an elongated structure having a generally elliptical longitudinal cross-sectional profile (which is truncated at one end). The dispenser 600 has a housing 602 that extends from a closed end 601 (which can be conceptually considered as a proximal end) and a dispensing end 603 (which can be conceptually considered as a distal end). The closed end 601 of the housing 602 is tapered in shape. The closed end 601 is specifically tapered and contoured to flushly form the proximal end 512 of the toothbrush 500 when the dispenser 600 is in the storage state. In other words, the outer surface of the closed end 601 is shaped to be flush with the outer surfaces of the flanges 514 and extend beyond the ends of the flanges 514 (shown in FIGS. 1 and 2). The dispensing end 603 of the housing 602 is shaped to abut the protrusion 552, 553 of the handle 510 of the toothbrush 500 when the dispenser is in the storage state (as in FIG. 8). The abutment of the dispensing end 603 of the housing 602 against the protrusion 552, 553 is preferably such that the cavity 551 (which houses the applicator 605) is substantially enclosed and/or sealed so as prevent unwanted leaking and/or drying of the applicator 605.

The housing 602 can be of a single-layer or a multi-layer construction, and is preferably constructed of a material that is sufficiently rigid to provide the necessary structural integrity for the dispenser 600. For example, the housing 600 can be made out of a moldable hard plastic. Moldable thermoplastics are preferred. Suitable plastics include polymers and copolymers of ethylene, propylene, butadiene, vinyl compounds and polyesters such as polyethylene terephthalate. The chosen plastic(s), however, must be compatible with the oral care material that is to be stored within the dispenser 600 and should not be corroded or degraded by active agents. If desired, an outer layer of a soft resilient material, such as an elstomeric material, can be added (similar to the grip 511). Suitable elastomeric materials include thermoplastic elastomers (TPE) or other similar materials used in oral care products. The elastomeric material may have a hardness durometer measurement ranging between A13 to A50 Shore hardness, although materials outside this range may be used. A preferred range of the hardness durometer rating is between A25 to A40 Shore hardness. While an over-molding construction can be utilized, a suitable deformable thermoplastic material, such as TPE, may be formed in a thin layer and attached to the inner rigid layer with an appropriate adhesive or by other means.

The housing 602 forms an internal cavity 608 which acts as a liquid reservoir for holding the desired oral care material or product, which can be any active or inactive oral care material. The oral care material and/or its carrier may be in any form such as a solid or a flowable material including without limitation viscous pastes/gels or less viscous liquid compositions. Preferably, the oral care material is a flowable material having a low viscosity in preferred embodiments. Any suitable oral care material can be used in the present invention. For example, the oral care material can include whitening agents, including without limitation, peroxide containing tooth whitening compositions. Suitable peroxide containing tooth whitening compositions are disclosed in U.S. Pat. No. 7,557,936, issued Jul. 7, 2009, to the present assignee, the entirety of which is hereby incorporated by reference. While a tooth whitening agent and/or a tooth sensitivity agent is one of the preferred active agents in the present invention, any other suitable other care materials can be used with embodiments of the present invention and, thus, stored within the reservoir 608. Contemplated oral care materials can be an active or non-active ingredient, including without limitation, antibacterial agents; oxidative or whitening agents; enamel strengthening or repair agents; tooth erosion preventing agents; anti-sensitivity ingredients; gum health actives; nutritional ingredients; tartar control or anti-stain ingredients; enzymes; sensate ingredients; flavors or flavor ingredients; breath freshening ingredients; oral malodor reducing agents; anti-attachment agents or sealants; diagnostic solutions; occluding agents; anti-inflammatory agents; dry mouth relief ingredients; catalysts to enhance the activity of any of these agents; colorants or aesthetic ingredients; and combinations thereof. The oral care material in one embodiment is preferably free of (i.e., is not) toothpaste. Instead, the active agent is intended to provide supplemental oral care benefits in addition to merely brushing one's teeth. Other suitable oral care materials could include lip balm or other materials that are typically available in a semi-solid state.

In some embodiments, the materials useful in the oral care agent contained in the reservoir may include oral care compositions comprising a basic amino acid in free or salt form. In one embodiment, the basic amino acid may be arginine. Various formulations would be useful to supply the arginine to the user. One such oral care composition, e.g., a dentifrice; may be used comprising:

i. an effective amount of a basic amino acid, in free or salt form, e.g., arginine, e.g., present in an amount of at least about 1%, for example about 1 to about 30%; by weight of total formulation, weight calculated as free base;
 ii. an effective amount of fluoride, e.g., a soluble fluoride salt, e.g., sodium fluoride, stannous fluoride or sodium monofluorophosphate, providing from about 250 to about 25,000 ppm fluoride ions, e.g., about 1,000 to about 1,500 ppm; and
 iii. an abrasive, e.g., silica, calcium carbonate or dicalcium phosphate.

The dental treatment materials of the present invention preferably have a viscosity suitable for use in tooth treatment applications and methods. As used herein, the "viscosity" shall refer to "dynamic viscosity" and is defined as the ratio of the shearing stress to the rate of deformation as measured by AR 1000-N Rheometer from TA Instruments, New Castle, Del.

When measured at a shear rate of 1 seconds$^{-1}$, the viscosity preferably will have a range with the lower end of the range generally about 0.0025 poise, preferably about 0.1 poise, and more preferably about 75 poise, with the upper end of the range being selected independently of the lower end of the range and generally about 10,000 poise, preferably about 5,000 poise, and more preferably about 1,000 poise. Non-limiting examples of suitable viscosity ranges when measured at a shear rate of 1 seconds$^{-1}$ includes, about 0.0025 poise to about 10,000 poise, about 0.1 poise to about 5,000 poise, about 75 poise to about 1000 poise, and about 0.1 poise to about 10,000 poise.

When measured at a shear rate of 100 seconds$^{-1}$, the viscosity will have a range with the lower end of the range generally about 0.0025 poise, preferably about 0.05 poise, and more preferably about 7.5 poise, with the upper end of the range being selected independently of the lower end of the range and generally about 1,000 poise, preferably about 100 poise, and more preferably about 75 poise. Non-limiting examples of suitable viscosity ranges when measured at a shear rate of 100 seconds.sup.31 1 includes, about 0.0025 poise to about 1,000 poise, about 0.05 poise to about 100 poise, about 7.5 poise to about 75 poise, and about 0.05 poise to about 1,000 poise.

When measured at a shear rate of 10,000 seconds$^{-1}$, the viscosity will have a range with the lower end of the range generally about 0.0025 poise, preferably about 0.05 poise, and more preferably about 5 poise, with the upper end of the range being selected independently of the lower end of the range and generally about 500 poise, preferably about 50 poise. Non-limiting examples of suitable viscosity ranges when measured at a shear rate of 10,000 seconds$^{-1}$ includes, about 0.0025 poise to about 500 poise, about 0.05 poise to about 50 poise, about 5 poise to about 50 poise, and about 0.05 poise to about 500 poise.

Each of the formulations contains a viscosity agent that adjusts the viscosity of the formulation to a level which permits effective flow from the reservoir 608, through the delivery channel 610, and to the dispensing end 603. This agent may be water, thickeners or thinners. The viscosity should be adjusted in relationship to the dimensions of the delivery channel 610 (including length, internal transverse cross-sectional area, shape, etc.), the composition of the delivery channel 610 used (i.e., hollow channel, porous channel, etc.), and the amount of force available to move the formulations through the delivery channel 610.

The reservoir 608 is fluidly coupled to an applicator 605 which protrudes from the dispensing end 603 of the housing 602 by a delivery channel 610. The delivery channel 610 delivers the oral care material from the reservoir 608 to the applicator 605. The user then presses and/or rubs the applicator 605 against his/her teeth to apply the oral care material to the desired oral surface, such as the teeth, preferably after and/or before brushing. The application process is much like using a standard pen and/or marker. Of course, in some embodiments, a delivery channel may not be necessary or may merely be an extension of the reservoir or a space connecting the reservoir and the applicator (or an orifice in the dispensing end).

The applicator 605 is preferably constructed of bristles, a sponge material or a fibrillated material. Suitable bristles include any common bristle material such as nylon or PBT. The sponge-like materials can be of any common foam material such as urethane foams. The fibrillated surfaces can be comprised of various thermoplastics. In the use of a bristles, the delivery channel 610 will deliver the composition to near the ends of the bristles. Usually there will be a single delivery channel. For sponge and fibrillated surfaces there usually will be plurality of smaller diameter channels so as to more uniformly distribute the composition onto the user's teeth. In one embodiment, the fibrillated material will have an essentially planar surface that has a plurality of protruding fibrils up to about 3 millimeter in length. Such a fibrillated surface provides a mini-brush surface. The invention, however, is not so limited and the applicator 605 can be any surface that can apply a viscous substance onto the hard surface of teeth. In other embodiments, the applicator 605 can be any type of surface and/or configuration that can apply a viscous substance onto the hard surface of teeth, including merely an uncovered opening/orifice that is spatial communication with the oral care material to be applied by the user.

In one embodiment, the applicator 709 may be constructed of an elastomeric material, such as TPE, and simply include a passageway extending therethrough. Such an embodiment may be especially suited for applying oral care materials whose effectiveness is facilitated by being pressed into the tubules of the teeth, such as the composition described herein in detail above.

The delivery channel 610 can be a suitable sized tubular conduit having a hollow passageway or it can be constructed of a porous material. The mechanism of delivery of the oral care material from the reservoir 608 to the applicator 605 (which can be a mere orifice in the dispensing end) can be strictly by capillary action, a mechanical or chemical pumping action, compression/squeezing of the dispenser 600, gravity and/or combinations thereof. In one embodiment, at least a portion of the housing 601 can be constructed to be transversely deformable so that the user can squeeze the dispenser 600, thereby increasing the pressure inside reservoir 608 and forcing the oral care material outwards from the reservoir 308 through the applicator 605. In such an embodiment, a one-way valve may be built into the dispenser to allow air back into the reservoir so that the dispenser housing 601 resumes its uncompressed/un-deformed state after use. In other embodiments, a piston-like mechanism can be used to dispense the oral care material from the reservoir 608 to the applicator 605. Of course, other mechanisms and actions can be used to achieve the dispensing goal. In certain embodiments, the delivery channel 610 may further include a one-way valve that only allows the oral care material to flow from the reservoir 608 toward the applicator 605, thereby preventing saliva or other contaminants from being drawn from the applicator 605 back into the reservoir 608 and/or delivery channel 610.

In the illustrated embodiment of the dispenser 600, an overflow chamber 611 is created near the dispensing end 603 by the addition of a transverse wall 612. The transverse wall 612 separates and substantially seals the reservoir 608 from the overflow chamber 611. The delivery channel 610 extends through the transverse wall 612 and through the overflow chamber 611, thereby fluidly coupling the reservoir 608 to the applicator 609. A porous material, which is in the form of a sleeve 613 can be positioned within the overflow chamber 611. The overflow chamber 611 can minimize excessive amounts of the oral care material from reaching the applicator 605 or leaking from the dispenser 600. The overflow chamber 611 will not be needed in all embodiments of the dispenser, depending on the delivery mechanism used.

The details of the dispenser 600 described above are not to be considered limiting of the present invention unless specifically recited in the claims. It is to be understood that the structural details of the dispenser body and its fluid delivery system can vary greatly.

However, in one embodiment, in order to make the oral care system 400 user friendly for travel, the reservoir 608 and/or the volume of oral care material in the reservoir may be selected so that the oral care system 400 can be taken onto airplanes. Since about 2002, the volume of liquid that can be taken onto an airplane in the U.S. and other countries in a single container is limited, typically to about 3 fluid oz. It is preferred that the reservoir 608 and/or the volume of oral care material in the reservoir 608 be selected to meet the applicable regulatory standard, which may change from country to country and over time.

Furthermore, in some embodiments of the invention wherein the applicator 605 is an orifice, the applicator 605 will act like a nozzle or port for dispensing and/or ejecting a liquid or paste oral car agent/material to the desired oral surface. Such an arrangement is especially useful when combined with a compressible/squeezable dispenser housing. In embodiments where a semi-solid oral care material is used, such as lip balm sold under the tradename Chapstick®, the orifice may merely provide a passageway from the reservoir through which the semi-solid oral care material will protrude or can be slid.

In one embodiment, the housing 602 of the dispenser 600 may contain a gauge (not illustrated) that shows the user how much of the oral care material is left in the reservoir 608. In one embodiment, the gauge can be a transparent or translucent window built into the housing 602 of the dispenser that comprises indicia lines.

Figure 6:
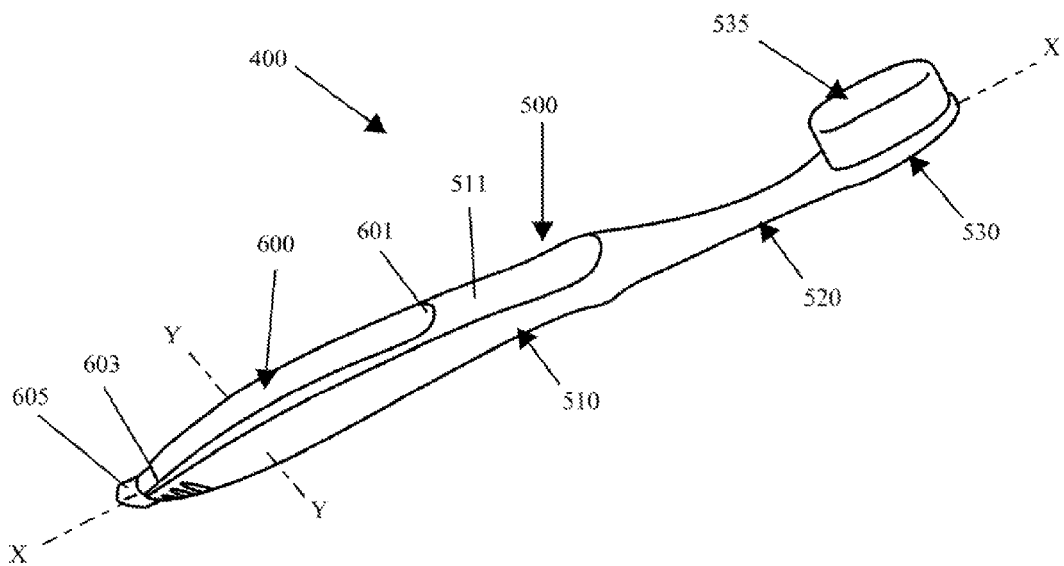
FIG. 6 is a front perspective view of the oral care system of FIG. 1, wherein the dispenser has been fully rotated into the application state.

The housing 602 of the dispenser 600 comprises opposing substantially planar lateral surfaces 621, a curved top surface 622 and a curved bottom surface 623. The curved top and bottom surfaces 622, 623 are convex in both the longitudinal and transverse directions and are contoured to form substantially flush surfaces with the outer surfaces 518 of the flanges 514 of the toothbrush 500. The curved top and bottom surfaces 622, 623 converge at the closed end 601 so as to form a rounded apex that acts as the proximal end 512 of the handle 510 of the toothbrush when the dispenser 600 is in the storage state. As will be discussed in greater detail below with respect to FIGS. 1-2 and 8-9, the housing 602 of the dispenser 600 is sized, shaped and contoured to flushly nest within the space 550 of the handle 510 of the toothbrush 500 so that the dispenser 600 inconspicuously forms a portion of the handle 510 and has an overall smooth contour both longitudinally and transversely Depressions 606 are formed into the planar lateral surfaces 621 of the housing 602. The depressions 606 are provided to mate with the protuberances 505 of the toothbrush 500 so that the dispenser can be pivotably mounted to the main body 516 of the toothbrush 500 so as to be rotatable back and forth between a storage state (FIG. 1) and an application state (FIG. 6). Preferably, the depressions 606 are provided in a middle portion 625 of the housing 600 (measured along its length). The middle portion 625 is preferably the middle fifty percent (50%) of the length of the housing 602 and more preferably the middle thirty-three percent (33%) of the length of the housing 602. Most preferably, the depressions 606 are located approximately at the middle point of the length of the housing 602. By positioning the depressions 606 (or other pivot structure) in the middle portion 625 of the housing 602, the dispenser 600 does not excessively protrude beyond the proximal ends 512 of the flanges 514 when the dispenser 600 is in the application state.

Referring now to FIGS. 1-2 and 8-9 concurrently, the oral care system 400 will be described when the dispenser 600 is in the storage state. When the dispenser 600 is in the storage state, the housing 602 of the dispenser 600 is nests within the space 550 formed between the flanges 514 and extends along the longitudinal axis X-X. The applicator 605 nests within the cavity 551 between top and bottom protrusion 552, 553. The dispensing end 603 of the dispenser 600 acts as a shoulder and abuts the top and bottom protrusion 552, 553 so as to substantially enclose and/or seal the cavity 551 with the applicator 605 therein. By enclosing and/or sealing the cavity 551, undesired leaking, bleeding and/or drying out of the applicator is minimized and/or eliminated. Additionally, the abutment contact between the dispensing end 603 of the dispenser 600 and the top and bottom protrusion 552, 553 retains the dispenser 600 in the storage state when subjected to normal ancillary forces imparted by a users palm and/or fingers during brushing. Contact between the applicator 605 and the top and bottom protrusion 552, 553 further assist in retaining the dispenser 600 in the storage state during brushing.

Alternatively, a cap could be secured to the dispensing end 603 of the housing 602 which may eliminate the need for sealing the cavity 551. In such an embodiment, one or both of the protrusions could 552, 553 could be omitted to allow the cap to pass into and out of the cavity 551 by rotation of the dispenser about axis Y-Y.

As mentioned above, the dispenser 600 nests within the space 550 of the handle 510 of the toothbrush 500 when in the storage state, the closed end 601 of the dispenser 600 forms the proximal end 512 of the handle 510 of the toothbrush. Additionally, the housing 602 of the dispenser 600 is flush with and forms a portion of the main body 516 of the handle 510 so that the handle 510 has smooth contours in all directions.

Figure 9:
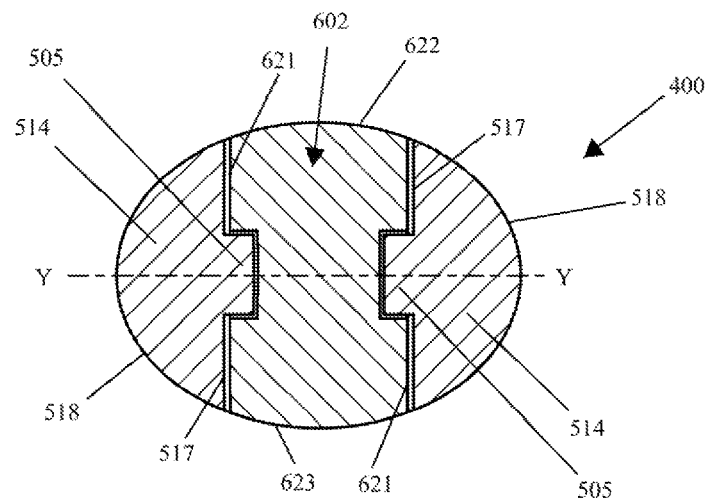
FIG. 9 is a transverse cross-sectional view of the oral care system of the present invention along line axis Y-Y of FIG. 1, wherein the dispenser is in the storage state.

As can beset be seen in FIG. 9, the top and bottom surfaces 622, 623 (which are convex in the transverse direction) of the housing 602 of the dispenser 600, in conjunction with the outer lateral surfaces 518 of the flanges 514, form an elliptical cross-sectional profile for the handle assembly. Preferably, the handle assembly (formed by the dispenser 600 and the main body 516) has a substantially elliptical transverse cross-sectional profile along its entire length.

Figure 5:
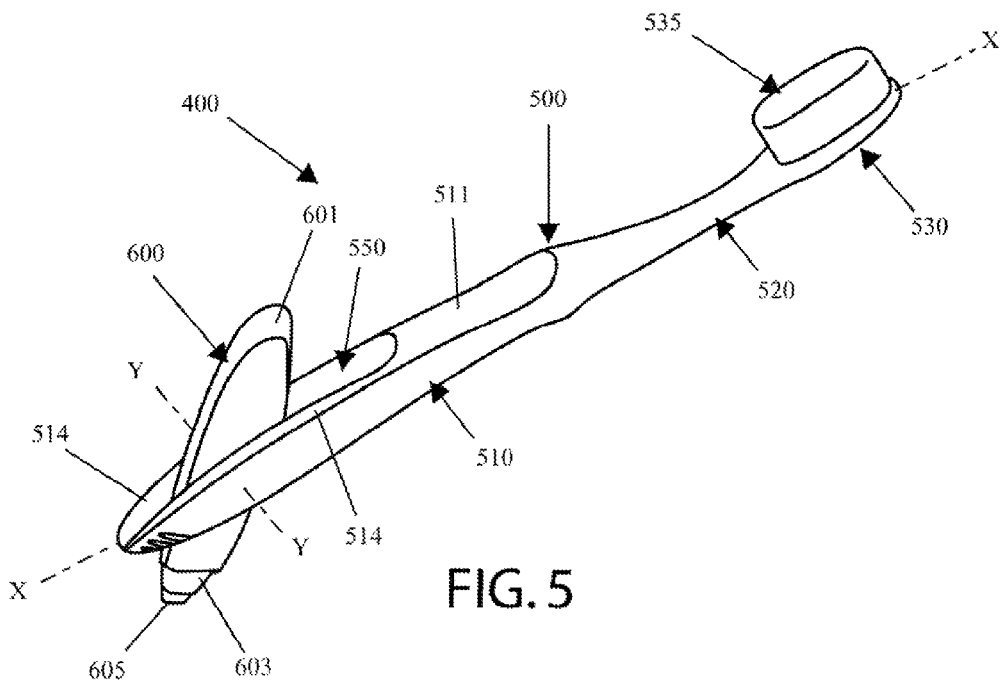
FIG. 5 is a front perspective view of the oral care system of FIG. 1, wherein the dispenser has been rotated out of the storage state toward the application state.
Figure 10:
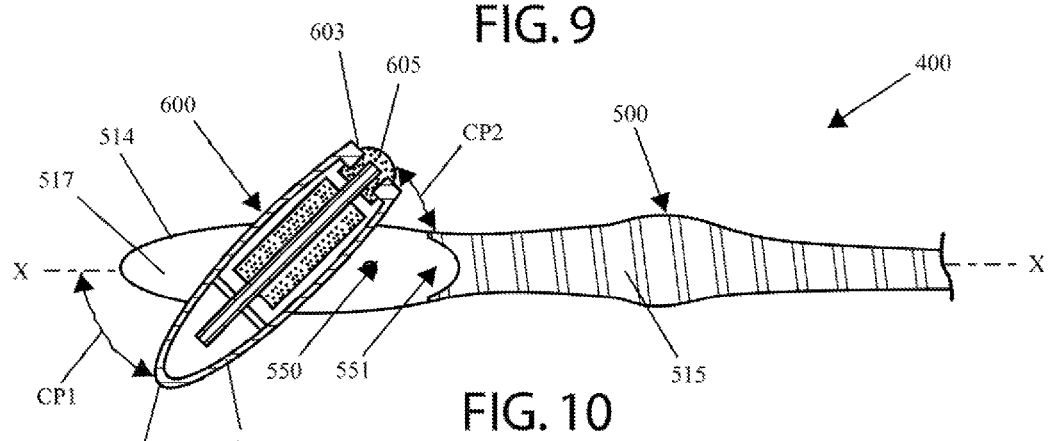
FIG. 10 is a longitudinal cross-sectional view of the oral care system of the present invention, wherein the dispenser has been rotated out of the storage state toward the application state.

Referring now to FIGS. 5 and 10 concurrently, the oral care system 400 is illustrated wherein the dispenser 600 has been rotated about axis Y-Y out of the storage state. In FIG. 5, the dispenser 600 has been rotated clockwise (with respect to the longitudinal axis X-X). In FIG. 10, the dispenser 600 has been rotated counter-clockwise (with respect to the longitudinal axis X-X). The direction of rotation is inconsequential to the invention.

As the dispenser 600 is initially rotated about axis Y-Y out of the storage state, the pressure exerted by the applicator 605 deforms the top or bottom protrusion 522, 523 until rotation is continued and the applicator 605 "snaps" past the top or bottom protrusion 522, 523. Alternatively, the applicator 605 can deform and/or bend.

As the rotation of the dispenser 600 about the axis Y-Y is continued, the closed end 601 of the dispenser 600 follows a first circumferential path CP1 that extends from the rear surface of the handle 510 while the dispensing end 603 of the dispenser 600 follows a second circumferential path CP2 that extends from the front surface of the handle 510. The rotation about axis Y-Y is continued until the dispenser 600 reaches the application state.

Figure 11:
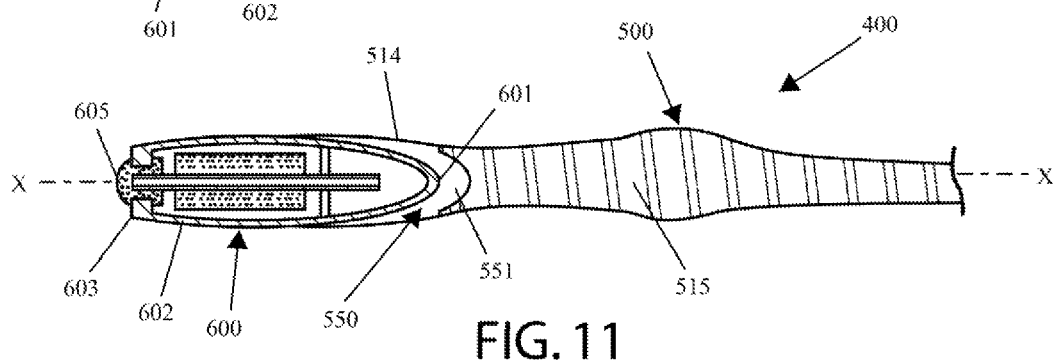
FIG. 11 is a longitudinal cross-sectional view of the oral care system of the present invention, wherein the dispenser has been fully rotated into the application state.

Referring now to FIGS. 6 and 11 concurrently, the oral care system 400 is illustrated wherein the dispenser 600 is in the application state. When in the application state, the dispenser 600 is aligned along the longitudinal axis X-X. The applicator 605 protrudes from the proximal end 512 of the toothbrush 500 so as to be easily used to apply the oral care material to the teeth (or other oral surface) of the user utilizing a pen-like technique. Even when in the application state, the housing 602 of the dispenser 600 nests within the space 550, resulting in a sleek and easy to use applicator. The angle of rotation about the axis Y-Y from the storage state to the application state is preferably about 180 degrees.

While not illustrated, it may be preferable for a locking mechanism and/or features be provided that will retain the dispenser 600 in the storage state when subject to forces experienced during the oral care material application process. For example, each of the planar inner surfaces 517 of the flanges 514 could be provided with a protrusion while the planar lateral surfaces 621 of the dispenser 600 could be provided with a corresponding indent for mating engagement. In one embodiment, the protrusions and indents could be hemi-spherical in shape. Of course other shapes and locking and/or stopping structures could be used to retain the dispenser 600 in the storage state. Additionally, if desired, the protrusion and/or indents can be properly located so that they also assist in retaining the dispenser 600 in the storage state during brushing.

Figure 12:
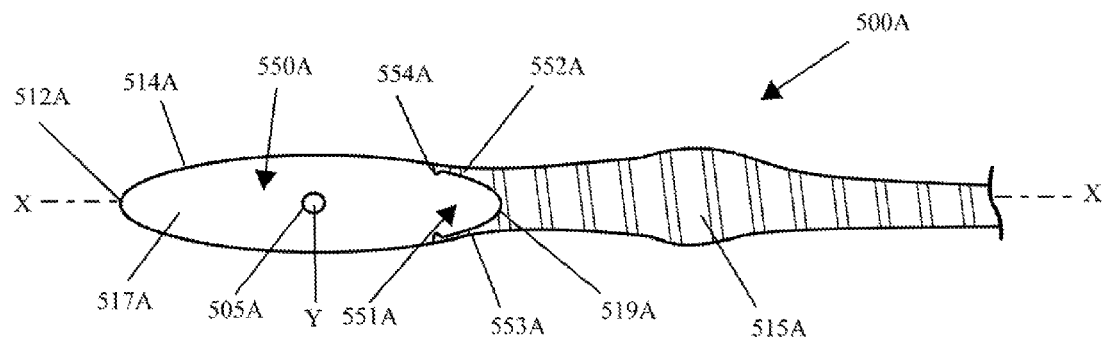
FIG. 12 is a longitudinal cross-sectional view of the handle portion of an alternative embodiment of a toothbrush of an oral care system according to the present invention.
Figure 13:
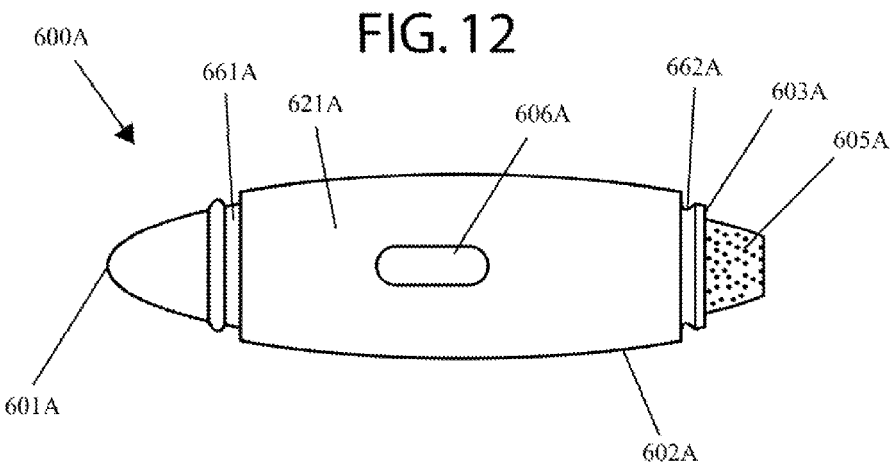
FIG. 13 is a side view of an alternative embodiment of a dispenser designed to be used in conjunction with the toothbrush of FIG. 12 to form an oral care system according to a second embodiment of the present invention.
Figure 14:
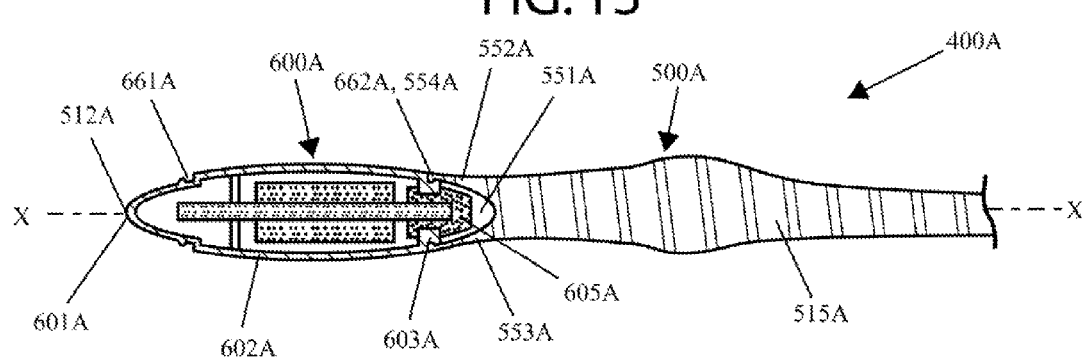
FIG. 14 is a longitudinal cross-sectional view of an oral care system incorporating the toothbrush of FIG. 12 and the dispenser of FIG. 13, wherein the dispenser is in the storage state.

Referring now to FIGS. 12 and 13 concurrently, alternative embodiment of a toothbrush 500A and a dispenser 600A are illustrated that can be used in combination to form an oral care system 400A according to a second embodiment of the present invention. The toothbrush 500A, the dispenser 600A, and the oral care system 400A are identical to that of the toothbrush 500, the dispenser 600, and the oral care system 400 discussed above with respect to FIGS. 1-11 with the exception that the pivot joint used to pivotably mount the dispenser 600A within the handle 510A of the toothbrush 500A is facilitates both relative translational movement and relative rotational movement between the dispenser 600A and the toothbrush 500A. Additionally, the dispenser 600 and toothbrush 500 are further adapted to retain the dispenser 600 in the storage and application states through improved mating engagement. In order to avoid redundancy, a detailed discussion of those components of the toothbrush 500A, the dispenser 600A, and the oral care system 400A that are substantially identical to that of the toothbrush 500, the dispenser 600, and the oral care system 400 is omitted. However, for reference and clarity, like numbers are used to identify like parts with the exception of the alphabetical suffix "A" being added.

The toothbrush 500A comprises top and bottom projections 552A, 553A. However, an annular ridge 554A projects from the inner surfaces of the top and bottom projections 552A, 553A and into the cavity 551A. As will be described below, it is not necessary for the top and bottom projections 552A, 553A to be deformable as the dispenser 600 is translated prior to (or after), rotation of the dispenser 600 to slidably remove (or slidably insert) the applicator 605A from the cavity 551A. The cavity 551A is shaped slightly different to accommodate the differently shaped applicator 605A.

The dispenser 600 comprises an annular groove 661A in the housing 602A near the closed end 601A. Similarly, the dispensing end 603A of the housing 602A comprises an annular groove 662A. As will be described below, the annular grooves 661A, 662A are sized and shaped for slidable mating engagement and disengagement with the annular groove 554A of the toothbrush 500A to: (1) hermetically seal the cavity 551A (with the applicator 605A therein) when the dispenser 600A is in the storage state; (2) retain the dispenser 600A in the storage state; and (3) retain the dispenser 600A in the storage state. While a groove/ridge mating engagement assembly is exemplified, the invention is not so limited and other structural features and shapes can be used so long as adequate mating engagement is achieved, including without limitation protrusion/depression assemblies, tight fit assemblies, compression fittings and the like.

Additionally, the depressions 606A within the planar lateral surfaces 621A of the housing 602A are elongated slots (rather than circular). By making the depressions 606A elongated, the protuberances 505A of the toothbrush 500A can both translate and pivot when inserted within the depressions 606A. Thus, the protuberances 505A and the elongated depressions 606A form a joint that facilitates both rotational and translational movement of the dispenser 600A relative to the toothbrush 500A.

Figure 16:
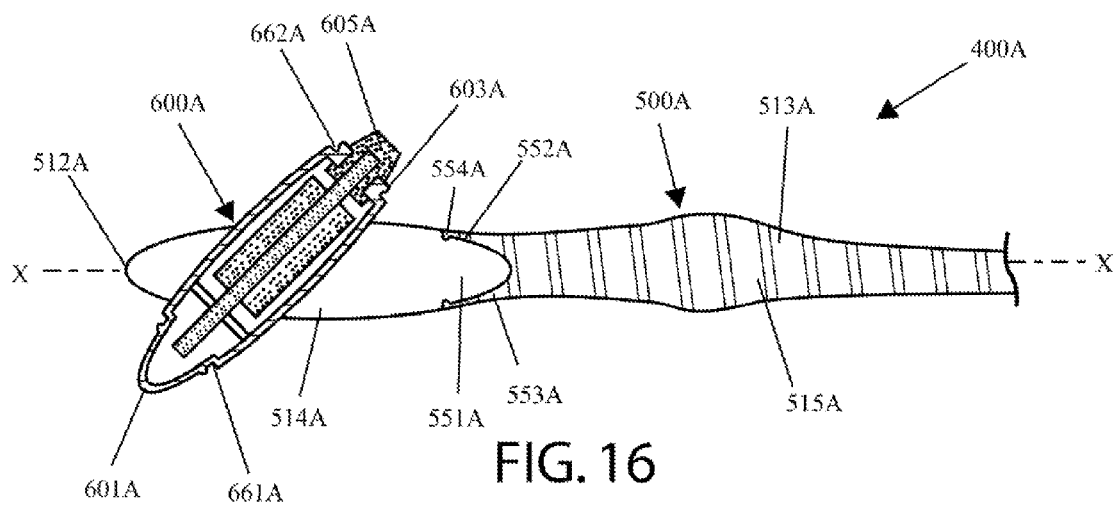
FIG. 16 is a longitudinal cross-sectional view of the oral care system of FIG. 15, wherein the dispenser has been rotated out of alignment with the longitudinal axis toward the application state.
Figure 17:
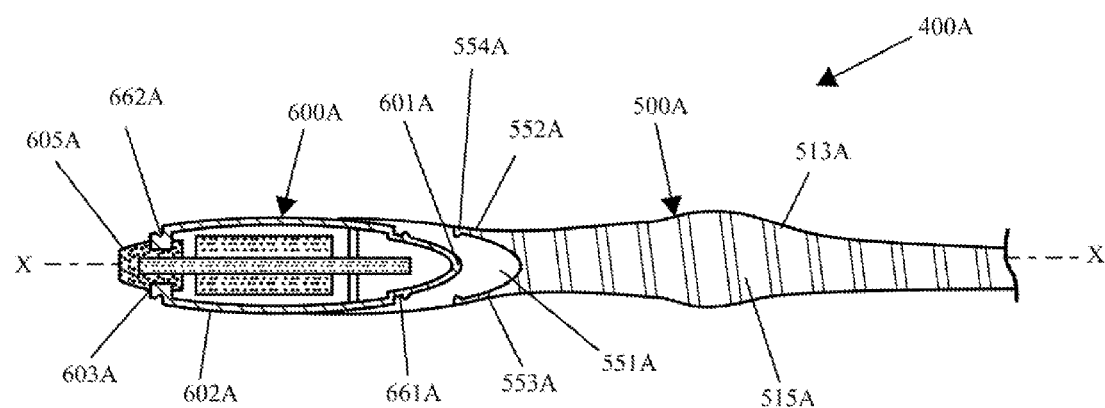
FIG. 17 is a longitudinal cross-sectional view of the oral care system of FIG. 16, wherein the dispenser has been rotated into alignment with the longitudinal axis with the applicator at the proximal end.
Figure 18:
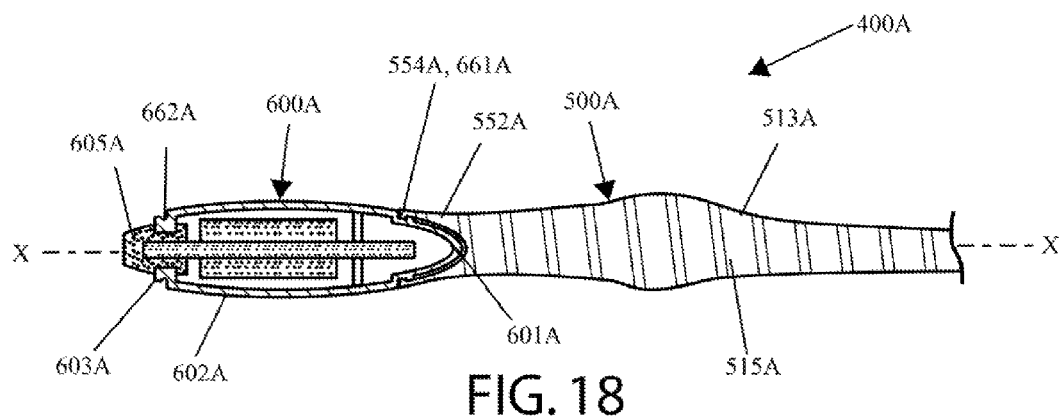
FIG. 18 is a longitudinal cross-sectional view of the oral care system of FIG. 17, wherein the dispenser has been translated into the storage state.

Referring now to FIGS. 14-18, the oral care system 400A will be described as the dispenser 600A is moved from the storage state (FIG. 14) to the application state (FIG. 18). Beginning with FIG. 14, the dispenser 600A is in the storage state wherein the dispenser 600A is aligned with the longitudinal axis X-X and the applicator 605A is fully nested within the cavity 551A. In the storage state, the annular ridge 554A of the toothbrush 500A is in mating engagement with the annular groove 662A at the dispensing end 603A of the dispenser 600A. The mating between the annular ridge 554A and the annular groove 662A is preferably such that it hermetically seals the cavity 551A, thereby preventing bleeding and drying up of the applicator 605A during periods of non-use. Additionally, the mating engagement between the annular ridge 554A and the annular groove 662A retains the dispenser 600A in the storage state when subjected to ancillary forces imparted by the user during a brushing or other oral care procedure.

Figure 15:
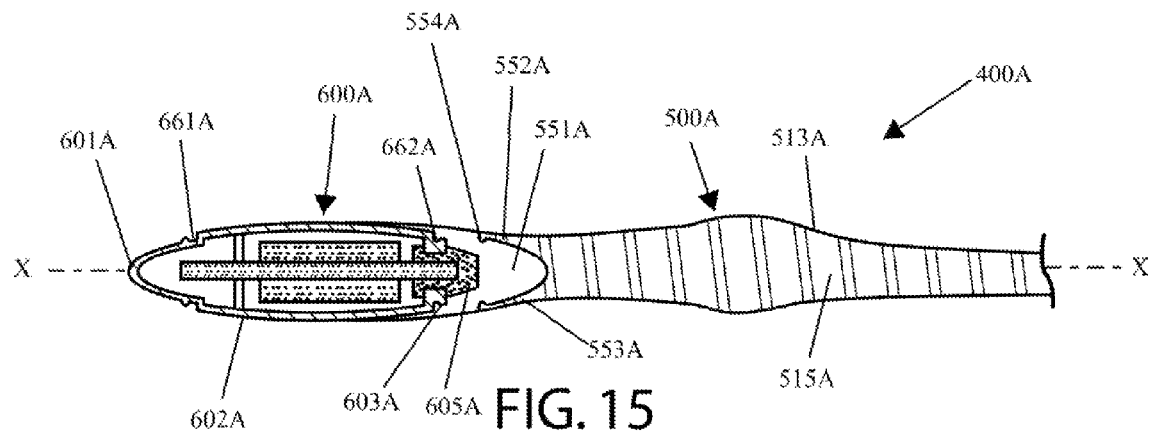
FIG. 15 is a longitudinal cross-sectional view of the oral care system of FIG. 14, wherein the dispenser has been translated along the longitudinal axis out of the storage state.

Turning now to FIG. 15, when the user desires to use the applicator, he/she applies force to the dispenser 600A to slidably translate the dispenser 600A along the longitudinal axis X-X away from the distal end 513A of the handle 510A (right to left in the illustration). As the dispenser 600A translates in a direction parallel with the longitudinal axis X-X, the annular groove 662A of the dispenser 600A and the annular ridge 554A of the toothbrush 500A disengage, allowing the dispenser 600A to translate unrestricted. The dispenser 600A is translated until the applicator 605A is sufficiently removed from the cavity 551A so that the applicator 605A does not contact the protrusions 552A, 553A during the subsequent rotation of the dispenser 600A. Stated another way, the dispenser 600A is translated until the applicator 605A is sufficiently removed from the cavity 551A so that it does not interfere and/or impede the rotation.

As shown in FIG. 16, as the rotation of the dispenser 600A is continued, the closed end 601A of the dispenser 600A follows a first circumferential path that extends from the rear surface of the handle 510A while the dispensing end 603A of the dispenser 600A follows a second circumferential path that extends from the front surface of the handle 510A.

Referring now to FIG. 17, the rotation of the dispenser 600A is continued until the dispenser 600A is again aligned with the longitudinal axis X-X and the applicator 605A is extending from the proximal end 512A of the toothbrush 500A. Again, this is about 180 degrees of rotation.

Referring now to FIG. 18, once the dispenser is aligned as shown in FIG. 17, the dispenser 600A is translated toward the distal end 513A of the handle 510A in a direction parallel to the longitudinal axis X-X (left to right in the illustration). This translation continues until the annular groove 661A of the dispenser 600A mates with the annular ridge 554A of the toothbrush 500A. This mating help retain the dispenser 600A in the storage state. At this stage, the closed end 601A of the dispenser 600A is nested within the cavity 551A.

While a number of embodiments of the current invention have been described and illustrated in detail, various alternatives and modifications will become readily apparent to those skilled in the art without departing from the spirit and scope of the invention. As various changes could be made in the above methods, compositions and structures without departing from the scope of the invention, it is intended that all matter contained in this application, including all mechanisms and/or modes of interaction described above, shall be interpreted as illustrative only and not limiting in any way the scope of the appended claims.

What is claimed is:

1. An oral care system comprising:
 a toothbrush comprising a head, a handle and one or more tooth engaging elements extending from the head;
 the handle having a distal end, a proximal end and a longitudinal axis;
 the handle of the toothbrush comprising a main body and a dispenser pivotably mounted to the main body;
 the dispenser including a housing having a first end and a second end, a reservoir located within the housing containing an oral care material, and an applicator at the second end of the housing for dispensing the oral care material from the reservoir;
 the main body including a base portion at the distal end of the handle and first and second flanges extending from the base portion to the proximal end of the handle, the first and second flanges extending along the longitudinal axis in a spaced apart manner so that a space is formed between an inner surface of the first flange and an inner surface of the second flange;
 the head connected to the base portion of the handle at the distal end; and
 the dispenser pivotably mounted between the first and second flanges within the space, the dispenser pivotable between: (i) a storage state wherein the applicator of the dispenser is nested within the main body; and (ii) an application state wherein the applicator is exposed for oral care use.

2. The oral care system of claim 1 further comprising the dispenser pivotably mounted to the first and second flanges at a middle portion of the housing of the dispenser, wherein as the dispenser is pivoted between the storage state and the application state, the second end of the dispenser follows a first circumferential path extending from one side of the handle and the second end of the dispenser follows a second circumferential path extending from an opposite side of the handle.

3. The oral care system of claim 1 further comprising:
the first end of the dispenser forming the proximal end of the handle in the storage state; and
the applicator extends from the proximal end of the handle in the application state.

4. The oral are system of claim 1 further comprising wherein when the dispenser is in the storage state, the dispenser is flushly positioned between the flanges so that the handle has a substantially smooth contour.

5. The oral care system of claim 4 further comprising:
the first flange having an outer surface and the second flange having an outer surface;
the dispenser having a top surface and a bottom surface; and
when the dispenser is in the storage state, the top and bottom surfaces of the dispenser are flush with the outer surfaces of the first and second flanges.

6. The oral care system of claim 5 further comprising:
the outer surfaces of the first and second flanges being transversely convex;
the top and bottom surfaces of the dispenser being transversely convex; and
when in the storage state the handle has a substantially elliptical transverse cross-section taken at a longitudinal position through the dispenser and the first and second flanges.

7. The oral care system of claim 1 further comprising:
the dispenser having, lateral surfaces that oppose the inner surfaces of the first and second flanges in the storage state; and
the inner surfaces of the first and second flanges having one of a protrusion or an indent and the lateral surfaces of the dispenser having the other of the protrusion or the indent that mates with the protrusion or the indent of the first and second flanges in the storage state, thereby maintaining the dispenser in the storage state when subjected to forces applied by a user during brushing.

8. The oral care system of claim 1 wherein the dispenser has a substantially elliptical longitudinal cross-sectional profile that is truncated at the second end.

9. The oral care system of claim 1 further comprising the dispenser being pivotably and translationally mounted to the first and second flanges.

10. The oral care system of claim 1 further comprising:
the base portion having a cavity for receiving the applicator; and
the dispenser being pivotably and translationally mounted to the first and second flanges so as to be capable of translating between: (i) a first position wherein the applicator is within the cavity of the of the base portion; and (ii) a second position wherein the applicator is at least partially removed from the cavity of the base portion so that the applicator does not interfere, with the dispenser being pivoted, between the application state and the storage state.

11. The oral care system of claim 10 further comprising the housing of the dispenser contacting the base portion when the dispenser is in the first position, thereby sealing the cavity with the applicator located therein.

12. A combined toothbrush and oral care material dispenser comprising:
a toothbrush comprising:
a handle having a proximal end, a distal end and a longitudinal axis; and
a head connected to the distal end of the handle, the head including one or more tooth engaging elements extending from the head;
a dispenser including:
a housing having a dispensing end and a closed end;
a reservoir located within the housing, the reservoir containing an oral care material; and
an applicator at the dispensing end of the housing and in communication with the reservoir for dispensing the oral care material;
the handle having an elongated slot extending along the longitudinal axis; and
the dispenser pivotably mounted to the handle within the slot, the dispenser pivotable between: (i) a storage state wherein the applicator of the dispenser is nested within the handle; and (ii) an application state wherein the applicator is exposed for oral care use.

13. The oral care system of claim 12 wherein the elongated slot extends through the handle from one lateral surface of the handle to the opposite lateral surface of the handle.

14. The oral care system of claim 13 wherein the one lateral surface of the handle is a front surface of the handle and the opposite lateral surface of the handle is a rear surface of the handle.

15. The oral care system of claim 14 further comprising the dispenser pivotably mounted to the handle at a middle portion of the housing of the dispenser, wherein as the dispenser is pivoted between the storage state and the application state, the dispensing end of the dispenser follows a first circumferential path extending from the one lateral surface of the handle and the closed end of the dispenser follows a second circumferential path extending from the opposite lateral surface of the handle.

16. The oral care system of claim 12 further comprising:
the closed end of the dispenser forming the proximal end of the handle in the storage state; and
the applicator extending from the proximal end of the handle in the application state.

17. The oral care system of claim 12 further comprising the dispenser being pivotably and translationally mounted to the handle.

18. The oral care system of claim 12 further comprising:
the handle having a cavity for receiving the applicator; and
the dispenser being pivotably and translationally mounted to the handle so as to be capable of translating between: (i) a first position wherein the applicator is within the cavity; and (ii) a second position wherein the applicator is at least partially removed from the cavity so that the applicator does not interfere with the dispenser being pivoted between the application state and the storage state.

19. The oral care system of claim 18 further comprising the housing of the dispenser contacting the handle when the dispenser is in the first position, thereby sealing the cavity with the applicator located therein.

20. The oral care system of claim 12 wherein the volume of the reservoir is designed to hold equal to or less than a volume of liquid permitted on airplanes in a single container by applicable regulations.

21. An oral care system comprising:
- an ansate oral care implement comprising a head, a handle having a longitudinal axis, and one or more oral surface engaging elements on the head;
- a dispenser mounted to a portion of the handle and having a reservoir containing an oral care material and an elastomeric applicator for dispensing the oral care material from the reservoir and applying the oral care material to an oral surface of a user;
- wherein the handle has a substantially elliptical transverse cross-sectional profile taken at a longitudinal position through the dispenser and the portion of the handle; and
- wherein an outer surface of the portion of the handle forms a convex portion of the substantially elliptical transverse cross-sectional profile and an outer surface of the dispenser forms the remainder of the substantially elliptical transverse cross-sectional profile.

22. The oral care system of claim 21 wherein the portion of the handle comprises a first flange and a second flange.

23. The oral care system of claim 21 wherein the dispenser is pivotably mounted to the handle at a middle portion of the dispenser between a storage state and an application state, wherein as the dispenser is pivoted between the storage state and the application state, a first end of the dispenser follows a first circumferential path extending from one lateral surface of the handle and a second end of the dispenser follows a second circumferential path extending from an opposite lateral surface of the handle.

24. The oral care system of claim 21 wherein when the dispenser is mounted to the portion of the handle, the dispenser is flushly positioned within the handle in both the transverse and longitudinal directions.

25. A method of applying an oral care material to an oral surface comprising:
- a) providing an ansate oral care implement comprising a head, a handle having a longitudinal axis, and one or more oral surface engaging elements, a dispenser having a reservoir containing the oral care material and an elastomeric applicator for dispensing the oral care material from the reservoir, the dispenser mounted to a portion of the handle wherein the handle has a substantially elliptical transverse cross-sectional profile taken at a longitudinal position through the dispenser and the portion of the handle; and wherein an outer surface of the portion of the handle forms a convex portion of the substantially elliptical transverse cross-sectional profile and an outer surface of the dispenser forms the remainder of the substantially elliptical transverse cross-sectional profile;
- b) contacting the oral surface with the oral surface engaging elements while the dispenser is mounted to the portion of the handle and the elastomeric applicator is nested within the handle;
- c) manipulating the dispenser so that the elastomeric applicator is un-nested from the handle; and
- d) applying the oral care material to the oral surface through contact with the elastomeric applicator.

26. The method of claim 25 wherein the oral surface are teeth.

27. The method of claim 25 wherein the dispenser is pivotably mounted to the portion of the handle, and wherein step c) comprises pivoting the dispenser from a storage state to an application state.

28. The method of claim 25 wherein the care material is a tooth whitening agent or a tooth sensitivity agent.

* * * * *